US012569149B2

(12) United States Patent
Paradis et al.

(10) Patent No.: US 12,569,149 B2
(45) Date of Patent: Mar. 10, 2026

(54) SYSTEM AND METHOD TO DETECT THE PRESENCE AND PROGRESSION OF DISEASES CHARACTERIZED BY SYSTEMIC CHANGES IN THE STATE OF THE VASCULATURE

(71) Applicant: The Trustees of Dartmouth College, Hanover, NH (US)

(72) Inventors: Norman Alan Paradis, Putney, VT (US); Ryan J. Halter, Orford, NH (US); Jonathan T. Elliott, Plainfield, NH (US); Vikrant S. Vaze, Hanover, NH (US); Ethan K. Murphy, White River Junction, VT (US)

(73) Assignees: The Trustees of Dartmouth College, Hanover, NH (US); Mary Hitchcock Memorial Hospital, for itself and on behalf of Dartmouth-Hitchcock Clinic, Lebanon, NH (US)

( * ) Notice: Subject to any disclaimer, the term of this patent is extended or adjusted under 35 U.S.C. 154(b) by 39 days.

(21) Appl. No.: 18/028,532

(22) PCT Filed: Sep. 27, 2021

(86) PCT No.: PCT/US2021/052241
§ 371 (c)(1),
(2) Date: Mar. 25, 2023

(87) PCT Pub. No.: WO2022/067204
PCT Pub. Date: Mar. 31, 2022

(65) Prior Publication Data
US 2023/0355109 A1 Nov. 9, 2023

Related U.S. Application Data

(60) Provisional application No. 63/083,563, filed on Sep. 25, 2020.

(51) Int. Cl.
A61B 5/02 (2006.01)
A61B 5/00 (2006.01)
A61B 5/0536 (2021.01)

(52) U.S. Cl.
CPC ........ *A61B 5/02042* (2013.01); *A61B 5/0075* (2013.01); *A61B 5/0536* (2013.01);
(Continued)

(58) Field of Classification Search
CPC . A61B 5/0075; A61B 5/02042; A61B 5/0536; A61B 5/0537; A61B 5/14542;
(Continued)

(56) References Cited

U.S. PATENT DOCUMENTS 9,719,842 B2 8/2017 Paradis
2007/0246046 A1 10/2007 Teschner
(Continued)

FOREIGN PATENT DOCUMENTS

WO 2019245163 12/2019

OTHER PUBLICATIONS

Weinstein et al., "Analyzing Big Data with Dynamic Quantum Clustering", 2013 (Year: 2013).*
(Continued)

*Primary Examiner* — Christopher L Cook
(74) *Attorney, Agent, or Firm* — Loginov & Associates, PLLC; William A. Loginov

(57) ABSTRACT

This invention provides a system and method that employs multiple measurements of various, relevant tissue states of a patient to detect and predict OH and similar conditions. These multi anatomic measurements are transformed by a multivariate algorithm to outputs that convey the diagnostic and prognostic risk of the disease of interest. This novel, multiple-measurement technique avoids use of a single measurement, which is generally unlikely to adequately
(Continued)

extract sufficient information to drive a clinically useful test in the setting of complex system disease. The system and method herein thereby allows automated monitoring of currently stable patients who, are known or suspected to have OH and/or similar internal conditions on a substantially continuous basis.

20 Claims, 15 Drawing Sheets

(52) U.S. Cl.
CPC .......... *A61B 5/7264* (2013.01); *A61B 5/7275* (2013.01); *A61B 5/6823* (2013.01); *A61B 5/6824* (2013.01); *A61B 5/6828* (2013.01)

(58) Field of Classification Search
CPC . A61B 5/14552; A61B 5/6823; A61B 5/6824; A61B 5/6828; A61B 5/6831; A61B 5/7225; A61B 5/7264; A61B 5/7275; A61B 8/0833; A61B 8/085; A61B 8/0858; A61B 8/4416; A61B 8/5223
See application file for complete search history.

(56) References Cited

U.S. PATENT DOCUMENTS

| | | |
|---|---|---|
| 2013/0225985 A1 | 8/2013 | Ross |
| 2015/0032750 A1 | 1/2015 | Weinstein |
| 2017/0336247 A1 | 11/2017 | Paradis |
| 2018/0000405 A1 | 1/2018 | Penders |
| 2018/0317859 A1 | 11/2018 | Kohli |
| 2020/0174517 A1* | 6/2020 | Martinez ................ G01S 19/01 |
| 2020/0196962 A1 | 6/2020 | Zhao |
| 2020/0293882 A1 | 9/2020 | Liu |

OTHER PUBLICATIONS

Awad, A. A. et al. Analysis of the ear pulse oximeter waveform. Journal of clinical monitoring and computing 20, 175-184 (Apr. 2006).

Baggerly, K. A., Morris, J. S. & Coombes, K. R. Reproducibility of SELDI-TOF protein patterns in serum: comparing datasets from different experiments. Bioinformatics 20, 777-785 (Jan. 2004).

Belle, A. et al. A signal processing approach for detection of hemodynamic instability before decompensation. PloS one 11, e0148544 (Feb. 2016). 20 pages.

Borsic, A., Halter, R., Wan, Y., Hartov, A. & Paulsen, K. D. Electrical impedance tomography reconstruction for three-dimensional imaging of the prostate. Physiological measurement 31, S1 (Jul. 2010). 17 pages.

Cannon, J. W. Hemorrhagic Shock. N Engl J Med 378, 370-379 (Jan. 25, 2018).

Convertino, V. A. Blood pressure measurement for accurate assessment of patient status in emergency medical settings. Aviation, space, and environmental medicine 83, 614-619 (Jun. 2012).

Convertino, V. A. et al. Use of advanced machine-learning techniques for noninvasive monitoring of hemorrhage. Journal of Trauma and Acute Care Surgery 71, S25-S32 (Jul. 2011).

Convertino, V. A., Wirt, M. D., Glenn, J. F. & Lein, B. C. The compensatory reserve for early and accurate prediction of hemodynamic compromise: a review of the underlying physiology. Shock 45, 580-590 (Jun. 2016).

Cooke, W. H., Ryan, K. L. & Convertino, V. A. Lower body negative pressure as a model to study progression to acute hemorrhagic shock in humans. Journal of Applied Physiology 96, 1249-1261 (Apr. 2004).

Delpy, D. T. & Cope, M. Quantification in tissue near-infrared spectroscopy. Philosophical Transactions of the Royal Society of London. Series B: Biological Sciences 352, 649-659 (Jun. 1997).

Diop, M., Elliott, J. T., Tichauer, K. M., Lee, T.-Y. & St. Lawrence, K. A broadband continuous-wave multichannel near-infrared system for measuring regional cerebral blood flow and oxygen consumption in newborn piglets. Review of Scientific Instruments 80, 054302 (May 2009). 9 pages.

Diop, M., Wright, E., Toronov, V., Lee, T.-Y. & Lawrence, K. S. Improved light collection and wavelet de-noising enable quantification of cerebral blood flow and oxygen metabolism by a low-cost, off-the-shelf spectrometer. Journal of biomedical optics 19, 057007 (May 2014). 11 pages.

Fantini, S. et al. Frequency-domain multichannel optical detector for noninvasive tissue spectroscopy and oximetry. Optical engineering 34, 32-43 (Jan. 1995).

Gesquiere, M. J. et al. Impact of withdrawal of 450 ml of blood on respiration-induced oscillations of the ear plethysmographic waveform. Journal of clinical monitoring and computing 21, 277-282 (Jun. 2007).

Golub, G. H. & Reinsch, C. Singular value decomposition and least squares solutions. in Linear Algebra 134-151 (Numerische Mathematik , Apr. 1970).

Kim, S.-H. et al. Accuracy and Precision of Continuous Noninvasive Arterial Pressure Monitoring Compared with Invasive Arterial Pressure A Systematic Review and Meta-analysis. The Journal of the American Society of Anesthesiologists 120, 1080-1097 (May 2014).

Krizhevsky, A., Sutskever, I. & Hinton, G. E. Imagenet classification with deep convolutional neural networks. in Advances in neural information processing systems 1097-1105 (Jan. 2012).

Leonarduzzi, R. F., Schlotthauer, G. & Torres, M. E. Wavelet leader based multifractal analysis of heart rate variability during myocardial ischaemia. in 2010 Annual International Conference of the IEEE Engineering in Medicine and Biology 110-113 (IEEE, Sep. 2010).

Li, T. & Zhou, M. ECG classification using wavelet packet entropy and random forests. Entropy 18, 285 (Aug. 2016). 16 pages.

Liu, F. T., Ting, K. M. & Zhou, Z.-H. Isolation forest. in 2008 Eighth IEEE International Conference on Data Mining 413-422 (IEEE, Dec. 2008).

Maharaj, E. A. & Alonso, A. M. Discriminant analysis of multivariate time series: Application to diagnosis based on ECG signals. Computational Statistics & Data Analysis 70, 67-87 (Sep. 2013).

Matcher, S. J. & Cooper, C. E. Absolute quantification of deoxyhaemoglobin concentration in tissue near infrared spectroscopy. Physics in Medicine & Biology 39, 1295 (Mar. 1994). 19 pages.

McGrath, S. P., Ryan, K. L., Wendelken, S. M., Rickards, C. A. & Convertino, V. A. Pulse oximeter plethysmographic waveform changes in awake, spontaneously breathing, hypovolemic volunteers. Anesthesia & Analgesia 112, 368-374 ( Feb. 2011).

Moody, G. B. & Mark, R. G. The impact of the MIT-BIH arrhythmia database. IEEE Engineering in Medicine and Biology Magazine 20, 45-50 (May/ Jun. 2001).

Murphy, E. K., Mahara, A. & Halter, R. J. A novel regularization technique for microendoscopic electrical impedance tomography. IEEE transactions on medical imaging 35, 1593-1603 (Jul. 2016).

Murphy, E. K., Mahara, A., Wu, X. & Halter, R. J. Phantom experiments using soft-prior regularization EIT for breast cancer imaging. Physiological measurement 38, 1262 (May 2017). 17 pages.

Murphy, E. K., Skinner, J., Martucci, M., Rutkove, S. B. & Halter, R. J. Toward Electrical Impedance Tomography Coupled Ultrasound Imaging for Assessing Muscle Health. IEEE transactions on medical imaging 38, 1409-1419 (Dec. 2018).

Parks, J. K., Elliott, A. C., Gentilello, L. M. & Shafi, S. Systemic hypotension is a late marker of shock after trauma: a validation study of Advanced Trauma Life Support principles in a large national sample. The American journal of surgery 192, 727-731 (Apr. 2006).

Pucci, O., Toronov, V. & Lawrence, K. S. Measurement of the optical properties of a two-layer model of the human head using broadband near-infrared spectroscopy. Applied optics 49, 6324-6332 (Nov. 2010).

Rokach, L. Ensemble-based classifiers. Artificial Intelligence Review 33, 1-39 (Nov. 2009).

(56) References Cited

OTHER PUBLICATIONS

Scheeren, T. W. L., Schober, P. & Schwarte, L. A. Monitoring tissue oxygenation by near infrared spectroscopy (NIRS): background and current applications. Journal of clinical monitoring and computing 26, 279-287 (Mar. 2012).

Selb, J., Zimmermann, B. B., Martino, M., Ogden, T. & Boas, D. A. Functional brain imaging with a supercontinuum time-domain NIRS system. in Optical Tomography and Spectroscopy of Tissue X vol. 8578 857807 (International Society for Optics and Photonics, Mar. 2013). 10 pages.

Shackelford, S. A. et al. Early identification of uncontrolled hemorrhage after trauma: current status and future direction. Journal of Trauma and Acute Care Surgery 77, S222-S227 (Apr. 24, 2014).

Soller, B. et al. Oxygen saturation determined from deep muscle, not thenar tissue, is an early indicator of central hypovolemia in humans. Critical Care Medicine 36, 176-182 (Jan. 2008).

Wan, Y. et al. Sensitivity study of an ultrasound coupled transrectal electrical impedance tomography system for prostate imaging. Physiological measurement 31, S17 (Jul. 2010). 14 pages.

Weinstein, M. Strange bedfellows: Quantum mechanics and data mining. Nuclear Physics B—Proceedings Supplements 199, 74-84 (Feb. 2010).

Weinstein, M., Heifetz, A. & Klann, R. Detection of nuclear sources in search survey using dynamic quantum clustering of gamma-ray spectral data. The European Physical Journal Plus 129, 239 (Nov. 2014).

Wo, C. C. et al. Unreliability of blood pressure and heart rate to evaluate cardiac output in emergency resuscitation and critical illness. Critical care medicine 21, 218-223 (Feb. 1993).

Yager, R. R. On the Dempster-Shafer framework and new combination rules. Information sciences 41, 93-137 (Mar. 1987).

Yeganeh, H. Z. et al. Broadband continuous-wave technique to measure baseline values and changes in the tissue chromophore concentrations. Biomedical optics express 3, 2761-2770 (Nov. 2012).

Zhao, Q. & Zhang, L. ECG feature extraction and classification using wavelet transform and support vector machines. in 2005 International Conference on Neural Networks and Brain vol. 2 1089-1092 (IEEE, Nov. 2005).

Soo-Yeon Ji, et al: "Wavelet based analysis of physiological signals for prediction of severity of hemorrhagic shock", Complex Medical Engineering, 2009. CME. ICME International Conference On, IEEE, Piscataway, NJ, USA, Apr. 9, 2009 (Apr. 9, 2009), pp. 1-6, XP032392804, DOI: 10.1109/ICCME.2009.4906672 ISBN: 978-1-4244-3315-5, Abstract; p. 2, right-hand column, paragraph 2; p. 4, left-hand column, paragraph 2, right-hand column, paragraph 1.

* cited by examiner

SYSTEM AND METHOD TO DETECT THE PRESENCE AND PROGRESSION OF DISEASES CHARACTERIZED BY SYSTEMIC CHANGES IN THE STATE OF THE VASCULATURE

STATEMENT REGARDING FEDERALLY SPONSORED RESEARCH OR DEVELOPMENT

This invention was made with government support under W81XWH-18-2-0076 awarded by the Defense Health Agency, Medical Research and Development Branch. The government has certain rights in the invention.

FIELD OF THE INVENTION

This invention relates to systems and methods for non-invasive detection of conditions within a patient's body using electronic and optical-based devices, and more particularly to systems and methods for detecting internal bleeding.

BACKGROUND OF THE INVENTION

Ongoing or "occult" hemorrhage (OH) is typically characterized by a slow, low-volume loss of blood from an affected region of the body, which can be difficult to detect using conventional techniques. Early detection of ongoing hemorrhage (OH) before onset of shock is a universally acknowledged unmet need in both trauma and surgery. See, by way of background, Shackelford, S. A. et al. Early identification of uncontrolled hemorrhage after trauma: current status and future direction. Journal of Trauma and Acute Care Surgery 77, S222-S227 (2014); and Parks, J. K., Elliott, A. C., Gentilello, L. M. & Shafi, S. Systemic hypotension is a late marker of shock after trauma: a validation study of Advanced Trauma Life Support principles in a large national sample. The American Journal of Surgery 192, 727-731 (2006). Delays in the detection of OH are associated with a failure to rescue, and there is a dramatic deterioration in prognosis once the onset of clinically frank shock has occurred. Thus, an early alert to the presence of OH with an acceptable rate of false-positives and false-negatives can potentially save countless lives, as resuscitative and operative interventions can be initiated before shock has caused vital organ injury. Moreover, the ability to detect OH readily and early can potentially save significant time, costs and effort by allowing medical resources to be applied more efficiently and accurately—which is the essence of precision medicine.

Additionally, the prognosis of OH patients worsens significantly if allowed to progress to clinical shock. Hemorrhagic shock is severe hypovolemia, and results in impaired oxygen delivery to tissues. If left untreated, it leads to organ injury and death. Currently, death from hemorrhage occurs in approximately 60,000 individuals per year in the United States, with trauma as the leading cause. Since many of these individuals are young, the number of years of life lost (YLL) is almost 2 million. The causes of hemorrhagic shock can vary greatly, including trauma, postpartum hemorrhage, gastrointestinal bleeding, perioperative hemorrhage, and rupture of aneurysms. With brief reference to the inventive system 100 in FIG. 1, described further below, the graph 110 (with relative blood loss along the horizontal axis and probability of hemodynamic instability (from approximately 0 to 100 percent) along the vertical axis) indicates that when OH is allowed to progress to a clinically evident hemodynamic response, the incidence of vital organ injury and death increases dramatically.

If rescue from shock is to be achieved, early recognition is essential. However, most individuals will have a compensatory response to hypovolemia that maintains normal blood pressure until more than 30% of total blood volume is lost. During earliest stages of hemodynamic instability a cascade of both adaptive and maladaptive changes occur, triggered by intravascular volume depletion and exacerbated by trauma-related tissue injury. A combination of hemostatic and fibrinolytic changes, in addition to the already mentioned compensatory mechanisms, occur resulting in coagulopathy, hypothermia and progressive acidosis. See, by way of background, Cannon, J. W., Hemorrhagic Shock. New England J. Med. 378, 370-379 (2018). In short, ongoing hemorrhage is a rapid multi-organ, multi-mechanistic process that nevertheless eludes detection based on a single specific symptom or sign, until a precipitous decline in patient status occurs.

It is generally acknowledged that no adequate solutions currently exist for early detection of OH before development of hemodynamic instability. It is widely appreciated that the classic medical vital signs (112 in FIG. 1) perform poorly until late in the progression to shock after traumatic injury. See, by way of background Wo, C. C., et al., Unreliability of blood pressure and heart rate to evaluate cardiac output in emergency resuscitation and critical illness. Critical Care Medicine 21, 218-223 (1993); Convertino, V. A. et al., Use of advanced machine-learning techniques for noninvasive monitoring of hemorrhage. Journal of Trauma and Acute Care Surgery 71, S25-S32 (2011). Currently available techniques, including intermittent vital sign monitoring, laboratory analysis, and single measurement devices have poor performance before clinically obvious physiologic distress. See, by way of background Wo, C. C. et al., Unreliability of blood pressure and heart rate to evaluate cardiac output in emergency resuscitation and critical illness. Critical Care Medicine 21, 218-223 (1993); Convertino, V. A., Blood pressure measurement for accurate assessment of patient status in emergency medical settings. Aviation, Space, and Environmental Medicine 83, 614-619 (2012). A further, particular, challenge in detecting and monitoring OH is the resource management associated with bedside vigilance, as clinicians need to prioritize patients who are already unstable. Patients may begin to manifest the early clinical signs of hemodynamic instability when no one is at their bedside. Current alarms only alert clinicians when parameters such as heart rate and blood pressure are well outside the normal range. Such changes occur only after a relatively large fraction of the circulating blood volume has been lost. Additionally, even with current alarm values being generally set relatively high and low, the vast majority of alarms in clinical settings are false and are ignored by the clinical staff.[1]

Occult hemorrhage and its progression to frank shock is a specific example of the broader category of systemic illnesses with pathophysiology based on changes in intravascular volume and the physical characteristic of tissues and organs. Other examples include sepsis, toxidromes, gastrointestinal leak disorders, impairments of cardiac function, and progression of respiratory viral syndromes, among others. In studying such conditions, it is contemplated that the physical measurements of tissues and organs that are diagnostic or prognostic in occult hemorrhage may also be adapted for utility in these other disease states.

By way of background, reference is made to U.S. Pat. No. 9,719,842, entitled METHOD FOR THE DISCOVERY, VALIDATION AND CLINICAL APPLICATION OF MULTIPLEX BIOMARKER ALGORITHMS BASED ON OPTICAL, PHYSICAL AND/OR ELECTROMAGNETIC PATTERNS, by Paradis, incorporated herein by reference as useful background information, which teaches that diagnostic and prognostic algorithms with optical or electromagnetic inputs may be developed based on the measurement of those inputs and the anatomic and temporal patterns among multiplex measurements.

While the promise of innovative noninvasive measurement has received significant attention, development of effective bedside technologies has thus far been limited and their performance disappointing. In 2014, Kim et al. stated that "The results from this meta-analysis found that inaccuracy and imprecision of continuous noninvasive arterial pressure monitoring devices are larger than what was defined as acceptable" and noninvasive blood pressure measurement is among the most fully developed of these technologies. See, by way of background, Kim, S. H. et al., Accuracy and Precision of Continuous Noninvasive Arterial Pressure Monitoring Compared with Invasive Arterial Pressure, A Systematic Review and Meta-analysis. The Journal of the American Society of Anesthesiologists 120, 1080-1097 (2014).

To date, the failure of noninvasive technologies in the early detection or diagnosis of complex disease states has been profound. Typically, patients presenting with possible life-threatening systemic disease processes are monitored only with intermittent traditional vital signs, electrocardiography, and oxygen saturation. None of these data streams have sufficient diagnostic or prognostic signal for early detection or prediction of progression towards deterioration. We believe that this failure reflects the limitations of univariate systems and measurements (i.e., a single sensor in a single-location), compounded by patient-to-patient variation in physiologic response. Such approaches sacrifice the entire diagnostic signal in anatomic-temporal patterns, which likely has significant discriminant power. They try to force all of the diagnostic performance out of measurement of only a small number of tissue or molecular states (i.e., the oxygenations state of hemoglobin in one location).

In retrospect, this broad failure may have been predictable. Complex organisms have significant intra-species variation. In human patients, there is the additional variance resulting from acute and chronic comorbidities. Measurement of single biomarkers—including vital signs, standard measurements of organ function, and even serum chemistries—has failed to discover any single measurement whose clinical performance is currently acceptable for actual patient care.

SUMMARY OF THE INVENTION

This invention overcomes disadvantages of the prior art by providing a system and method that employs multiple measurements of electromagnetic and optical signals in multiple anatomic locations of a patient to detect OH and other systemic conditions. This novel, multiple-measurement technique avoids the limitations previously identified when using only a single physical measurement at one anatomic location, which is generally unlikely to adequately extract sufficient information to drive a clinically useful test in the setting of complex system disease, using even the most sophisticated signal processing and machine learning. The system and method herein thereby allows automated monitoring of currently stable patients, who are known or suspected to have OH and/or other systemic conditions, on a substantially continuous basis. Such automated monitoring leaves clinicians free to focus their efforts on patients already unstable and in need of attention. It is contemplated that the system and method herein can be targeted toward a variety of etiologies, although the described system and method described herein is, by way of an example, targeted towards OH—at a phase during which progression is not clinically manifest because it is not yet associated with clinically manifest symptoms/or signs.

In an illustrative embodiment, the system and method provides a multiplex (i.e multivariable) system capable of measuring electromagnetic and optical properties of tissues at multiple physiologically distinct anatomic locations. By way of a non-limiting example the electromagnetic measurement can be based upon one or more types of electrical impedance, and the optical measurement can be based upon near-infrared spectroscopy (NIRS). Physiologically distinct anatomic locations can include, but are not limited to, the thorax, the abdomen, the liver, the spleen, the cranium, or the extremities, among others.

In an illustrative embodiment, a system and method for detecting an internal condition in a living organism provides a plurality of wearable sensors that each respectively generate one or more types of sensor data with respect to the status of tissues, organs, or organ system functions, in which each of the wearable sensors being constructed and arranged to respectively provide a data stream to a processor so that polyanatomic patterns can be derived. A data analysis process running on the processor enters the data streams into a model, algorithm or equation and provides an output indicative and predictive of the presence or absence an internal condition or disease state. Illustratively, the internal condition is related to ongoing occult hemorrhage (OH). At least one of the wearable sensors can comprise an electrical impedance spectroscopy (EIS) sensing belt having a NIRS module integrated therewith to deliver both EIS and NIRS data relative to a contacted skin location on the body to the data stream. At least one of the wearable sensors can measure a form of electrical impedance. Illustratively, the data stream further includes information from at least one of: classic vitals, photoplethysmography or an electrocardiogram (ECG).

By way of illustration without limitation, the device may measure impedance at one or more locations. An already derived algorithm may combine the impedance data stream with one or more physiologic measurements including, but not limited to, data streams obtained from the electrocardiogram or pulse oximeter. The algorithm may output a result interpretable as the probability of a disease state. The device may alarm if the probability exceeds a predefined threshold.

The data analysis process can further include a supervised or unsupervised machine learning (for example, principal component analysis, neural networks, support vector machines, ensemble learners such as random forest or gradient boosting or machine learning such as convolutional neural networks or recurrent neural networks such as long short-term memory) processor that performs feature extractions and thereby generates metaclassifiers. The neural network can comprise at least one of a CNN, an RNN, and an LSTM. In a particular exemplary implementation, the machine learning processor can employ a powerful processor/algorithm, based, for example upon a neural network, such as a convolutional neural network (CNN), or an ensemble learner such as gradient boosting combined with metaclassifiers such as majority voting. The system and method can further provide a refining process that increases accuracy of the data stream based upon priors. Illustratively, the data analysis process can be constructed and arranged to operate multiple analysis processes concurrently, in which each of the analysis processes is adapted to provide optimized performance in each of multiple, discrete different risk categories, respectively. The analysis process can include a clinician-selectable process adapted to provide varying sensitivity and specificity. The system and method can include a system output display that shows a combination of analysis process results and the actual multiplex measurements that are inputs to the analysis process, both plotted against time. A medical treatment method can be provided in accordance with the system and method above. The treatment method can include application of the wearable sensors to the body at predetermined locations, including the thorax and limbs, and operation of the sensors and the processor on a substantially continuous basis to generate the output. The internal condition can be related to occult hemorrhage, an infectious process, or cardiovascular dysfunction.

BRIEF DESCRIPTION OF THE DRAWINGS

The invention description below refers to the accompanying drawings, of which.

DETAILED DESCRIPTION

I. System Overview

Figure 1:
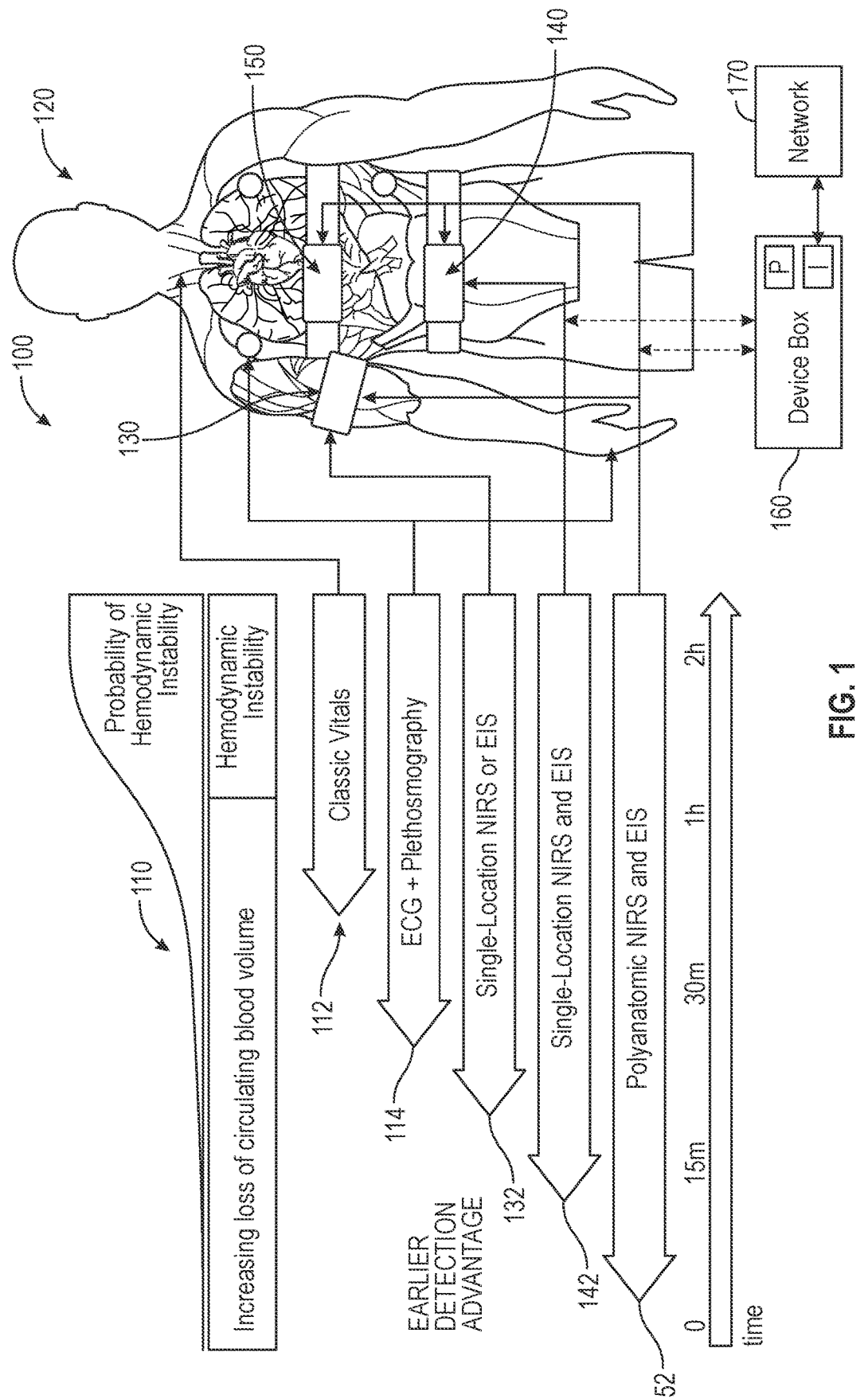
FIG. 1 is a diagram of an exemplary patient's body with associated sensors applied thereto, with associated data forms provided thereby, in a system and method for detecting internal conditions according to an illustrative embodiment.

Reference is made to FIG. 1, which shows an overall schematic representation 100 of the system and method for detecting OH and similar internal condition in a patient's (subject's) body 120. These data demonstrate the earlier detection of progression that is obtainable in multi-technology, polyanatomic approaches according to the embodiments herein. The diagram/representation 100 shows the location relative to the body 120 of known sensors and sensing arrangements/modalities in comparison with the classic vitals 112 and ECG/pleth uniplex systems 114, which are employed in the standard clinical environment. As shown, such techniques can allow for detection in the range of 30 minutes to 1 hour, when successful. According to the novel system and method herein, the traditional sensing modalities, and associated results, (112 and 114) can be substituted with, or supplemented by, additional sensing arrangements/modalities 130, 140 and 150. As described below, these sensing arrangements employ sensor assemblies that are removably applied to the patient using removable straps, or another attachment mechanism (e.g., removable adhesive, tape, etc.). By way of a non-limiting example, these sensors 130, 140 and 150 operate to produce additional data/results 132, 142 and 152, as shown, which can effectively reduce the detection time for OH and other similar conditions to less than 15 minutes. More particularly, a sensor 130 placed around an arm (e.g., a bicep) of the patient's body 120 can be adapted to produce single-location NIRS or EIS results 132. A sensor 140, located with around the abdomen, can also produce additional, single-location NIRS and EIS results 142. A combination of a sensor 150 placed around the chest, and the arm sensor 130, can produce polyanatomic NIRS and EIS results. Overall, the system and method features polyanatomical multiplex device deployment and feature recognition, which advantageously increases the probability of detecting, which likewise helps to avoid, hemodynamic instability—and which may otherwise exist in one or more single-location sensing arrangements.

II. Sensing Techniques and Results

A. Overall Arrangement

The system and method employs a multiplex, (as opposed to a uniplex) approach to instrumentation that provides additional predictive power that interoperates with machine learning methods. Multiplex can be defined similarly to multivariate, in that this approach employs measurement of multiple physical parameters at more than one anatomic location. This allows diagnostic and prognostic signal to be obtained from the multivariate relationships between the different sensing technologies, the anatomic patterns, and the temporal patterns.

Figure 2:
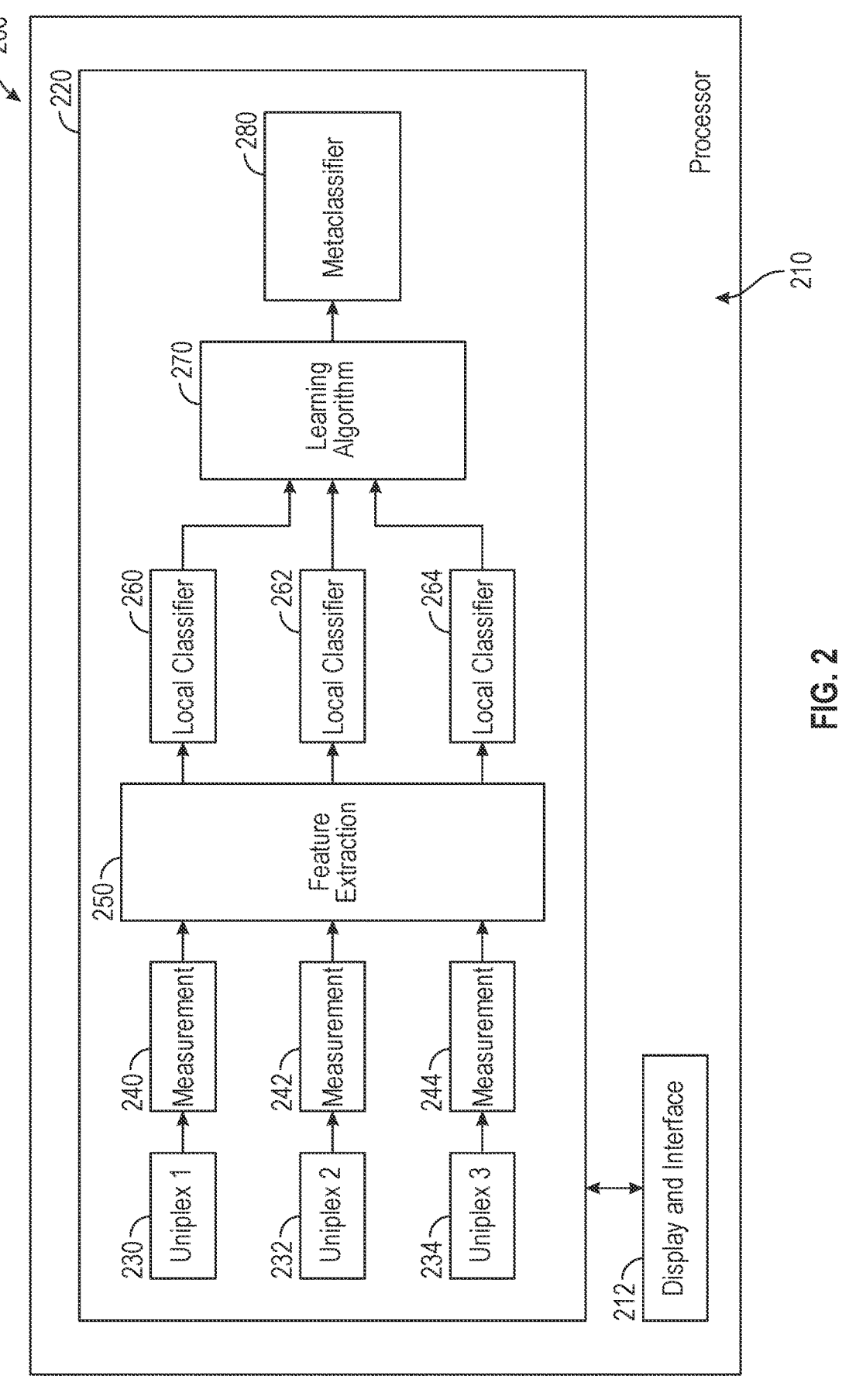
FIG. 2 is a block diagram showing a machine-learning-based, distributed classification process, and associated system processor for use in the system and method of FIG. 1.

More particularly, the sensor arrangement employs a modified NIRS approach, so that signals from the muscle and signals from subcutaneous fat and skin are separated and quantified in terms of underlying chromophores or optical properties. Note that the use of ultrasound sensing techniques to assist such separation and quantification can be appropriate. Additionally, EIT and EIS can be employed by the sensing arrangement(s) so that polyanatomical signals are synchronized and synergistically combined to be sensitive to both superficial and deep physiological changes associated with OH. Since the system and method provides substantially improved, multiplexed instrumentation, it can include supervised and unsupervised methods for machine learning, feature extraction and classification (see FIG. 2, described below). Additionally, Dynamic Quantum Clustering can be employed to avoid common pitfalls in large dimension data analysis. The above implementations can be reduced, by the system and method, to multianatomic, small form-factor fabricated device, which can be controlled by a single portable device box 160 (FIG. 1). This device can include one or more on-board and/or network-linked processing arrangement(s) P, as well as appropriate wired or wireless network interface(s) I for communicating with remote computing systems via one or more network(s) 170 (e.g., via LAN, WAN, etc.).

B. Multiplex Instrumentation

By way of further background, previous innovations in early detection of OH has fallen into two broad categories, namely, (a) a search to discover a single new measurement of tissue or organ status, or (b) application of machine learning and signal processing to existing single-sensor technologies. In general, such devices/approaches have failed to perform as intended and/or become adopted for use in the field. Measurement of single biomarkers—including vital signs, standard measurements of organ function, and even serum chemistries—has failed to discover any single measurement whose clinical performance was consistently actionable with respect to complex disease states. Optical or electromagnetic measurement and a single physiologic location has also had inadequate clinical performance. By way of background, it has been shown that a multivariable system can accurately indicate ongoing loss of central venous volume in a Lower Body Negative Pressure (LBNP) model. See Belle, A. et al., A signal processing approach for detection of hemodynamic instability before decompensation. PloS one 11, e0148544 (2016); Cooke, W. H., Ryan, K. L. & Convertino, V. A., Lower body negative pressure as a model to study progression to acute hemorrhagic shock in humans. Journal of Applied Physiology 96, 1249-1261 (2004). The illustrative system and method herein employs various teachings described therein when integrating multiple sensing technologies and locations via multivariable machine learning. Hence, the system and method can effectively utilize a broad set of potential noninvasive technologies, including various inexpensive, clinically and commercially validated off-the-shelf technologies, such as ECG and/or NIRS measurement of tissue oxygenation and impedance cardiography/tomography/spectroscopy. In addition to direct and indirect measurement of primary parameters, we also evaluate synthetically derived secondary and tertiary variables based on variability and waveform analysis. See, by way of background, Scheeren, T. W. L., Schober, P. & Schwarte, L. A., Monitoring tissue oxygenation by near infrared spectroscopy (NIRS): background and current applications. Journal of Clinical Monitoring and Computing 26, 279-287 (2012).

C. Enhanced Preprocessing of NIRS and Electrical Impedance Signals

Figure 3:
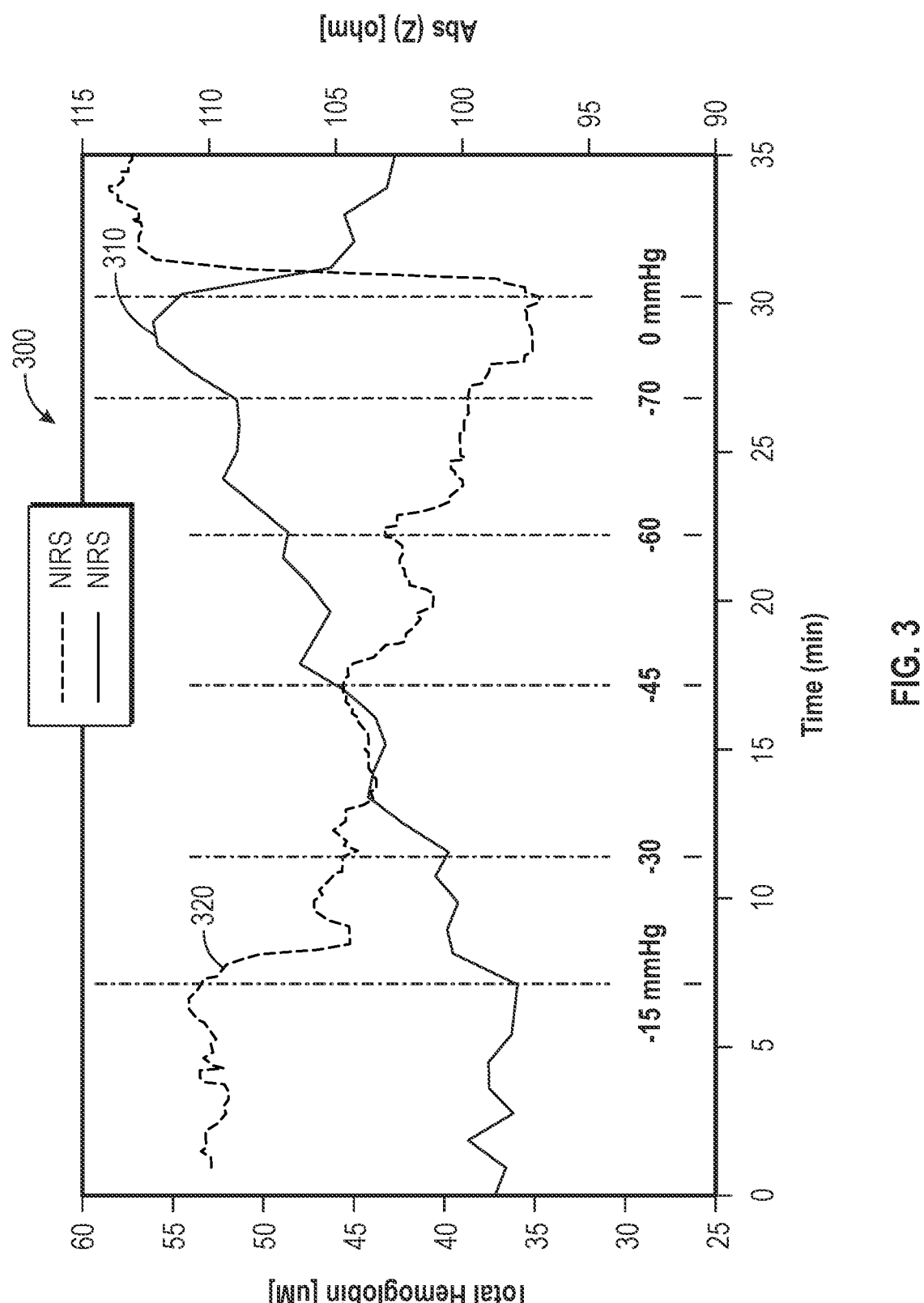
FIG. 3 is a graph showing results of thorax measurements obtained with NIRS and EIS on a human subject during a lower-body negative pressure experiment.

The system and method herein takes into account quantification of chromophores using (by way of non-limiting example) depth-resolved second derivative (of the image over time) near-infrared spectroscopy. Note that other techniques for quantifying chromophores should be clear to those of skill, including, but not limited to, applying first derivative spectroscopy, applying modelling approaches based upon absorption and scatter and/or various approximations to a diffusion equation. Moreover, a common challenge in applying machine-learning to signal feature extraction is a lack of attention given towards improvements in the instrumentation and data preprocessing that can provide more robust and relevant signals in the first place. It is contemplated that commercially available technologies can be refined so that the quality of the data streams are as high as possible. These challenges can include the inherent issue of Poisson-type noise in the spectroscopic data. An Anscombe transformation converts this to Gaussian white noise, and wavelet denoising filters it. See, by way of background, Diop, M., Wright, E., Toronov, V., Lee, T.-Y. & Lawrence, K. S., Improved light collection and wavelet de-noising enable quantification of cerebral blood flow and oxygen metabolism by a low-cost, off-the-shelf spectrometer. Journal of Biomedical Optics 19, 057007 (2014). These challenges also involve inherently large baseline variations in signal intensity due to coupling to skin, pigmentation, or loss due to scatter. Since these are first or second-order variations, a second derivative method can be applied to remove these sources of variability, allowing second order of chromophore basis spectra to be fit to the second derivative of attenuation. This allows a quantitative estimate of oxy- and deoxyhemoglobin to be obtained. A step-wise decrease in total hemoglobin that mirrors the increase in EIS due to reduced stroke volume can be seen during LBNP, as shown in the graph 300 of FIG. 3 showing a curve 310 of the EIS-based response and a curve 320 of NIRS-based response—and together comprising results of thorax measurements obtained with NIRS and EIS on a human subject during a lower-body negative pressure experiment. Note that NIRS is one of a variety of sensor types that can be employed to provide desired physiological data. It should be clear to those of skill that other types of electrical and/or optical-based sensing devices can be employed herein in a manner clear to those of skill.

Figure 4:
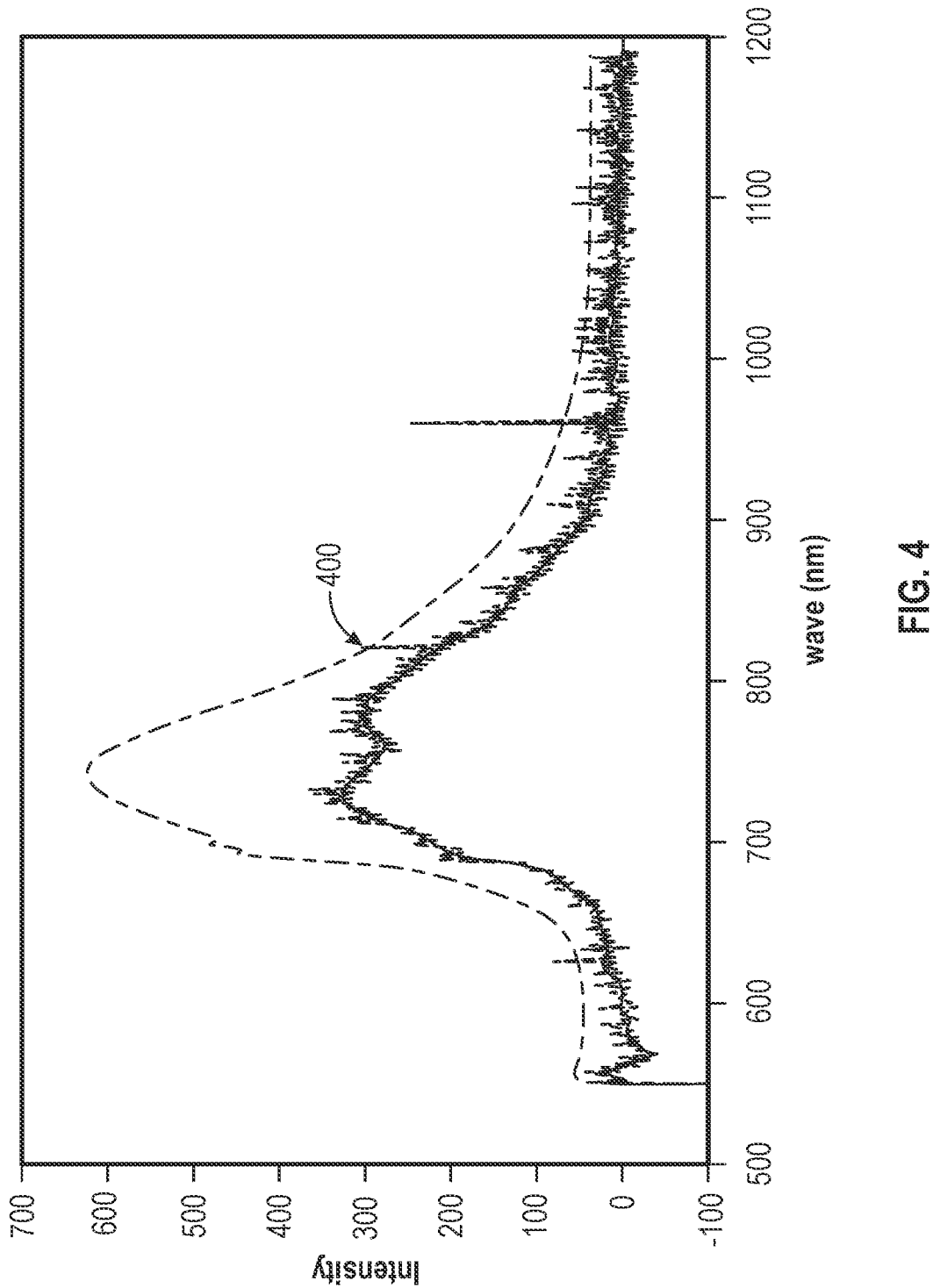
FIG. 4 is graph showing a NIRS denoised Light Emitting Diode (LED) reference signal and a comparison of raw and denoised intensity spectra acquired on an exemplary pig leg.
Figure 5:
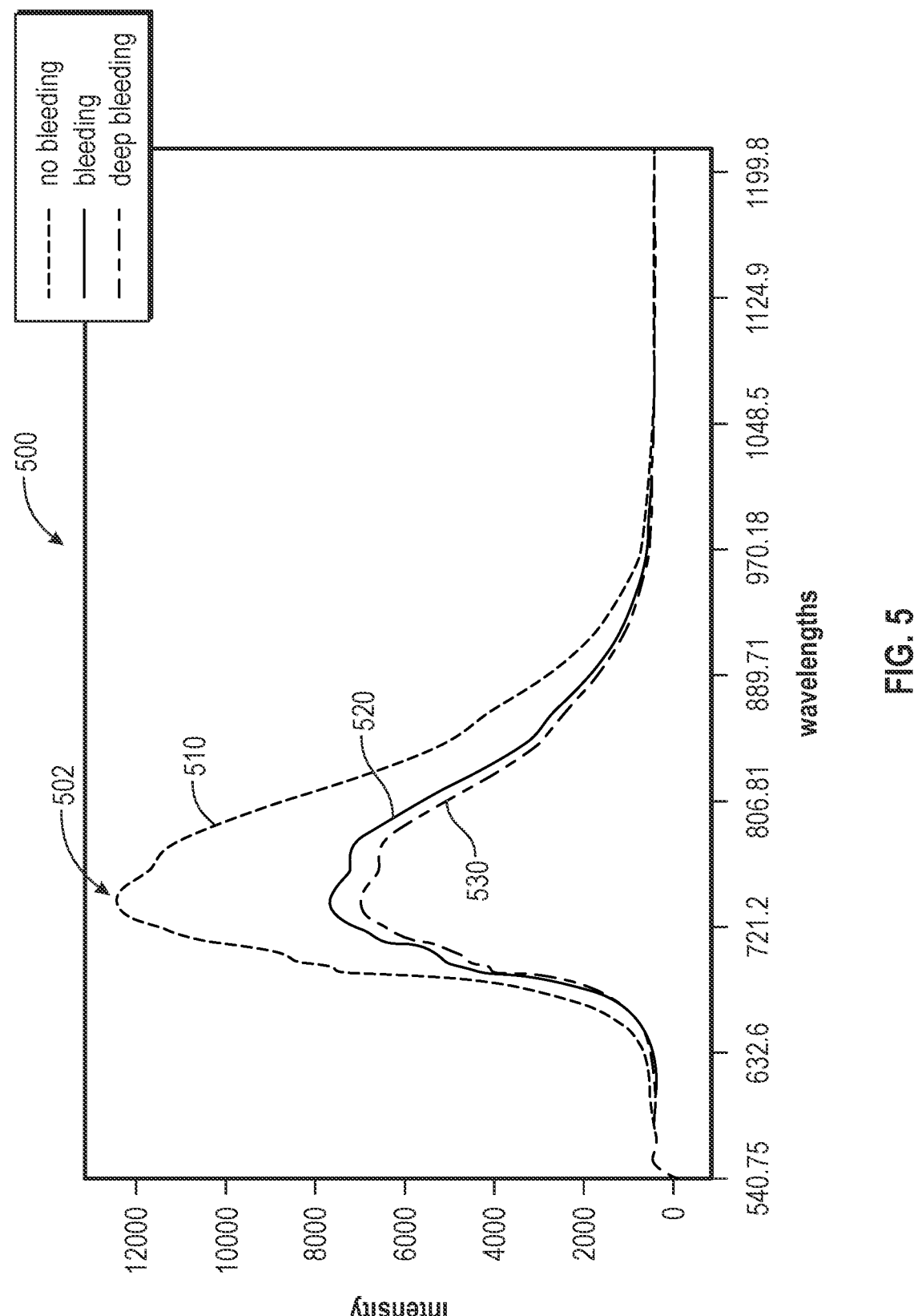
FIG. 5 is a graph showing a change in intensities detected from the head of a subject during three physiologic conditions, including no bleeding, moderate bleeding and deep bleeding.

It is recognized, in implementing the system and method herein that accurate preprocessing and denoising can significantly improve the quality of the NIRS features to be used for machine learning. Such preprocessing can potentially include the use of pixel-based based image processing and analysis. In particular, Compensatory Reserve Index (CRI) with which the ability of the body to compensate for blood loss can be detected. See, by way of background, Convertino, V. A., Wirt, M. D., Glenn, J. F. & Lein, B. C. The compensatory reserve for early and accurate prediction of hemodynamic compromise: a review of the underlying physiology. Shock 45, 580-590 (2016). The success of the CRI-based technique is attributed to the distinct changes in the arterial waveform between normal state and hypovolemia case such as hemorrhage. It has been recognized, that the experimentally generated NIRS signal, shown in the graph 400 of intensity versus wavelength in FIG. 4 provides a similar phenomenon to the Convertino reference. That is, the graph 400 shows NIRS denoised LED reference signal and a comparison of raw and denoised intensity spectra acquired on an experimental pig leg. Additionally, related FIG. 5 shows a graph 500 of the change in intensities (versus wavelength) detected from a patient's head during three physiologic conditions. Spectroscopic data can be analyzed using dimension reduction analysis, with different shapes around the peak 502. Notably, the curve 510 generated for no bleeding defines a significantly higher peak than the curve for moderate bleeding 520, which is slightly higher than the curve 530 for deep bleeding.

It is contemplated that signal analysis herein can further employ machine learning via, for example, two-dimensional convolutional neural networks (CNNs). CNNs are powerful image classification tools that do not overly rely on prepro- cessing steps such as feature extraction and noise filtering. Note that other forms of machine learning, and/or artificial intelligence (AI) techniques and algorithms can be employed in alternate implementations as well.

D. Supervised Learning Classifiers that Leverage Multiple Datasets

Advanced distributed and ensemble learning can be employed by the system and method. Ensemble techniques are described, by way of background, in Rokach, L. Ensemble-based classifiers. Artificial Intelligence Review 33, 1-39 (2010) and can include techniques such as Gradient Boosting (GB) and Random Forest (RF). These techniques have been found to experimentally enhance the accuracy of classifiers in preliminary machine learning analyses using the LBNP dataset and others. Reference is made again to FIG. 2, which shows an arrangement 200 for combining the knowledge from multiple machine learning-based classifiers in a distributed classification system 220. Such an arrange- ment 200 can be included in an on-board and/or remote computing system/processor 210, with an associated user interface and/or display (e.g., to program, control and review results of the process). An associated learning algorithm can be constructed based on Bayesian theory and the Dempster- Shafer framework, for example. See, by way of background, Yager, R. R., On the Dempster-Shafer framework and new combination rules. Information Sciences 41, 93-137 (1987). By way of a non-limiting example, the illustrative classifi- cation system 200 can consist of a plurality of uniplex inputs (1-N) 230, 232 and 234, that provide associated measure- ment data 240, 242 and 244 to a feature extraction process 250 implemented according to any acceptable technique. The feature extraction is followed by supervised learning to produce local classifiers 260, 262 and 264, each input to a meta-learning algorithm, which is used to generate a result- ing metaclassifier 280.

Note that machine learning, including, for example, LSTM (Long Short-Term Memory) Recurrent Neural Net- works can be employed with as part of the system and method herein.

E. Dynamic Quantum Clustering (DQC)

DQC can be employed in the system and method to address issues related to dimensionality. Numerical datasets are typically structured or conceptualized in a table. Each row of the table represents a single piece of numerical data (i.e., NIRS, EIS, or heart-rate data). The columns of the table provide the domain of definition of the features measured for each datum—which can comprise wavelengths, frequencies, or time steps. In clustering, it is desirable to determine which rows are more like one another (alike). However, the defi- nition of alikeness between items can be unclear. Thus, DQC treats each row of the table as a point in an n-dimensional space, where n is the number of columns in the table. By way of further background, see Weinstein, M., Heifetz, A. & Klann, R., Detection of nuclear sources in search survey using dynamic quantum clustering of gamma-ray spectral data. The European Physical Journal Plus 129, 239 (2014); Weinstein, M., Strange bedfellows: Quantum mechanics and data mining. Nuclear Physics B-Proceedings Supplements 199, 74-84 (2010). The Euclidean distance between the points is taken to be the measure of how alike two rows are. Hence, points that are near one another are more alike, and points that are far from one another are more different. For example, in the case of NIRS data the question is whether spectroscopic readings at times when a patient is not bleed- ing are more alike relative to each other, and less alike readings when a patient is bleeding.

With this definition of "alike", it is intuitive to consider a sub-region with many nearby points that are more like one another (i.e., a dense region) separated by less dense regions as clusters of points. Stated this way, the problem of finding rows of the spreadsheet that are more like one another amounts to finding all the regions with higher density. That is the problem DQC solves, no matter how many data points we have, and no matter how many features (columns) are in the spreadsheet. In this sense DQC can be thought of as a density-based clustering algorithm. There is well known problem associated with density-based clustering algo- rithms; namely, these algorithms suffer from the "curse of dimensionality". This means that typical density-based clus- tering algorithms perform more poorly as the dimension (or number of features) of the data goes up. DQC is unique in that it identifies regions of higher density using methods borrowed from quantum physics, instead of familiar math- ematical approaches. The unique properties of how quantum particles move in high dimension are what makes the density approach work in an efficient manner. DQC works by dividing the analysis into three steps: (a) use the data to create a function in the feature space that is an accurate proxy for density. By construction, this function goes down as the local density increases. For data with isolated clusters, dense regions correspond to local minima in the density function. However, for more complex data, where the den- sity of the data is constant along some one-dimensional shapes and falls off as one moves away from these shapes, then the density function will have multi-dimensional troughs. (b) DQC identifies clusters of data by identifying points that lie in the region of a local minimum, or trough. This is accomplished by moving the original data points in the direction of the nearest minimum. One might imagine that this could be accomplished using ordinary mathematics by moving data points downhill by using a variant of gradient descent; i.e., move a data point in small steps following the slope of the density function, thinking of the density function as a terrain map. A disadvantage to this approach is that it consumes significantly more computing time and resources as the number of dimensions increases and, in addition, it tends to involve a multiplicity of small local minima that should be ignored. (c) DQC operates to avoid the disadvantages caused by gradient descent by treating each data point as (e.g.) a localized quantum particle moving in a quantum potential defined to be the density function. Data points are then moved according to the rules of quantum evolution. DQC thereby successfully operates where other approaches fail because it can effectively lever- age non-locality and quantum tunneling to erase the effects of small, local minima.

III. Sensing Devices

A wearable sensing device (150 in FIG. 1) is provided as part of the system and method herein. A goal of such a device is enhancing and optimizing NIRS with improved spectral resolution. Optimization can be achieved in various ways, including, but not limited to the use of linear variable filters (LVFs) or a fiber-based approach. Where LVFs are employed, they can provide sufficient spectral resolution when coupled to a sensor as part of a fully enclosed, integrated unit with both a light source and a detector. In such an implementation, computer microcontrollers or FPGA components can be used to control and store data and work in tandem with many units. In an exemplary implementation, NIRS can be implemented using one or more broadband near infrared (NIR) LEDs in each sensor (e.g., an OSRAM SFH4736), and two optodes to collect reflectance measurements 1.0 and 2.5 mm apart. The optodes can be connected to their own spectrometer (e.g., FLAME from Ocean Optics). In an exemplary implementation, eight LEDs can be integrated into the circuit design so that two different long distances (L1 and L2) and two different short distances (S1 and S2) can be selected. For example, the source-detector distances will be as follows: L1=0.5 mm, L2=1.0 mm, S1=2.5 mm, S2=3.0 mm. The signal-to-noise ratio (SNR) can ultimately determine which pair of distances to use. The first LED can be centered at 750 nm (FWHM: 700 nm-825 nm) and a second LED can be centered around 635 nm (FWHM 100 nm). Either (a) a linear variable filter can be coupled to a linear charge-coupled device (CCD) sensor to provide a means of spectrally resolving the signal, or (b) a trifurcated fiber can be connected to each device and the distal end converging at the slit of a FLAME Ocean Optics Spectrometer. Power supply and PWM controllers are integrated into the device box, in the case of detector (a) all LEDs can be synchronized, in the case of (b) they can be multiplexed. These low footprint units can also contain the electrical impedance instrumentation.

Figure 6:
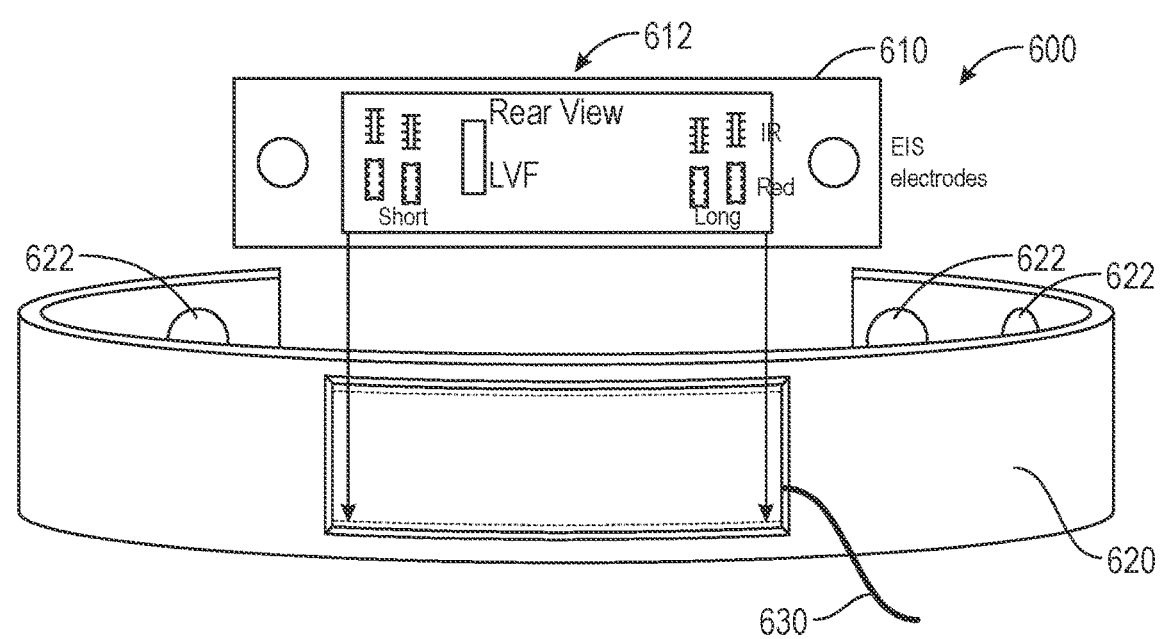
FIG. 6 is a diagram showing a wearable sensing device according to the system and method of FIG. 1, in which NIRS is integrated into an EIS belt, so as to deliver a combined data stream, which includes NIRS, EIS and Electrical Impedance Tomography (EIT) to the system processor.

With reference to the wearable sensor arrangement 600 FIG. 6, an NIRS device/module 610, with associated display 612, as described generally above is integrated into an EIS-sensing belt assembly 620. The belt assembly 620 includes internal wiring and circuitry that interconnects the skin-contacting EIS sensor pads 622. The belt 620 can include appropriate size-varying buckle arrangements or other mechanical coupling assemblies to maintain a snug fit against the patient. For example, the belt 620 can contain appropriate lengths of hook-and-loop fastener. An external lead 630 can exit the belt (and/or NIRS module 610) to carry data and power relative to a base station and/or other power and data-handling arrangement.

In an exemplary implementation, the sensing system can incorporate one or more types of electrical impedance measurements, in particular one or more of electrical impedance spectroscopy or electrical impedance tomography. It has been recognized via experimentation that such measurements are extremely sensitive to changes in intravascular volume, and can detect occult hemorrhage after only 1 percent to 3 percent loss in circulating blood volume (a relatively low quantity, physiologically). Measurements of one or more impedance types at more than one physiologically distinct anatomic location thereby allows for the use of machine learning derived pattern recognition as described herein. Hence, this combination results in previously unobtainable accuracy with Receiver Operating Characteristic-Area under the Curve (ROC-AUC) values in the range of 97% after just 20 minutes of low-flow occult hemorrhage.

Figure 7:
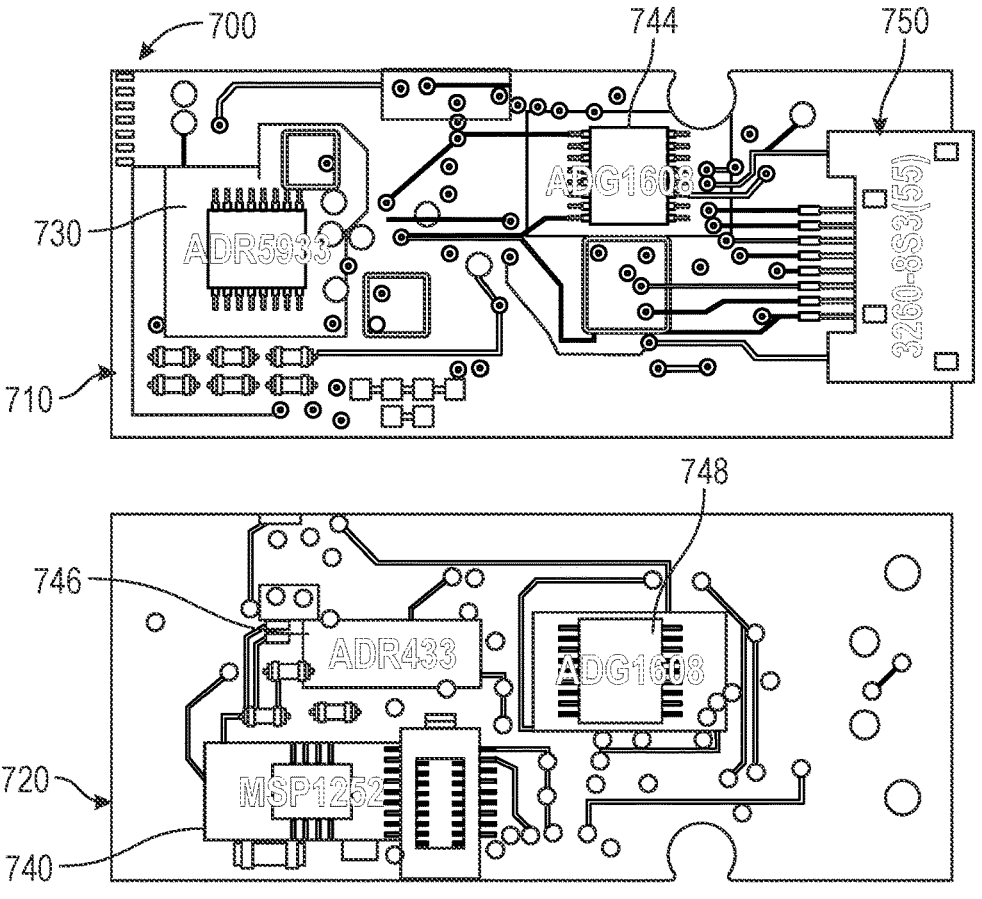
FIG. 7 is a diagram showing an impedance sensing circuit/module, implemented on a custom printed circuit board (PCB), with a multiplexed front-end that interfaces with our wearable sensing device of FIG. 6.

In an exemplary implementation, the sensing system can employ (e.g.) a customized, compacted circuit that operates in the manner of (e.g.) a commercially available 32-channel Sentech Pioneer system for EIT data acquisition and a 64-channel Sciospec system for EIS data acquisition at multiple anatomic sites (used by way of proof-of-concept experimentation herein). Such a custom, small-form-factor system can thereby provide both EIS and EIT capabilities in a single circuit (e.g., a printed circuit board (PCB)) solution to fit within our single-unit prototype. Such an exemplary PCB 700 is shown in FIG. 7 in both top view 710 and bottom view 720. This PCB 700 senses impedance with respect to the belt sensing pads 622 via a multiplexed front end. The EIS circuit board 700 thereby comprises a small form-factor printed circuit board (PCB) that can incorporate (e.g.) an AD5933 Network Analyzer integrated circuit (IC) (e.g., that are available from Analog Devices, Norwood, MA) 730. This IC records bipolar impedances over the frequency range of approximately 1 kHz to 100 kHz. In addition to this IC, the PCB can house a custom analog front-end circuit that can enable tetrapolar impedance measurements. This design can be based on previous designs reported in the literature. The impedance sensing circuits can be interfaced to a set of four (4) electrodes and interfaced to (e.g.) a low-power computing platform for system control, data analysis, and communication with additional peripherals 744, 746 and 748 (and connector 750). The computing platform can comprise any acceptable custom design of commercially available microcontroller, microprocessor, or similar circuit, including, but not limited to, the MSP430, MSP1252, etc., available from Texas Instruments.

In an exemplary implementation by way of illustration without limitation, the device may measure a type of electrical impedance at one or more locations and enhance the diagnostic performance by means of algorithmic combination of that signal with one or more other signals. The type of electrical impedance may be one or more of electrical: bioimpedance, impedance tomography, or impedance spectroscopy. An algorithm previously derived may combine the impedance data stream with one or more physiologic measurements including, but not limited to, data streams obtained from the electrocardiogram or pulse oximeter. The algorithm may output a result interpretable as the current or future probability of a disease state. The device may alarm if the probability exceeds a predefined threshold.

Figure 8:
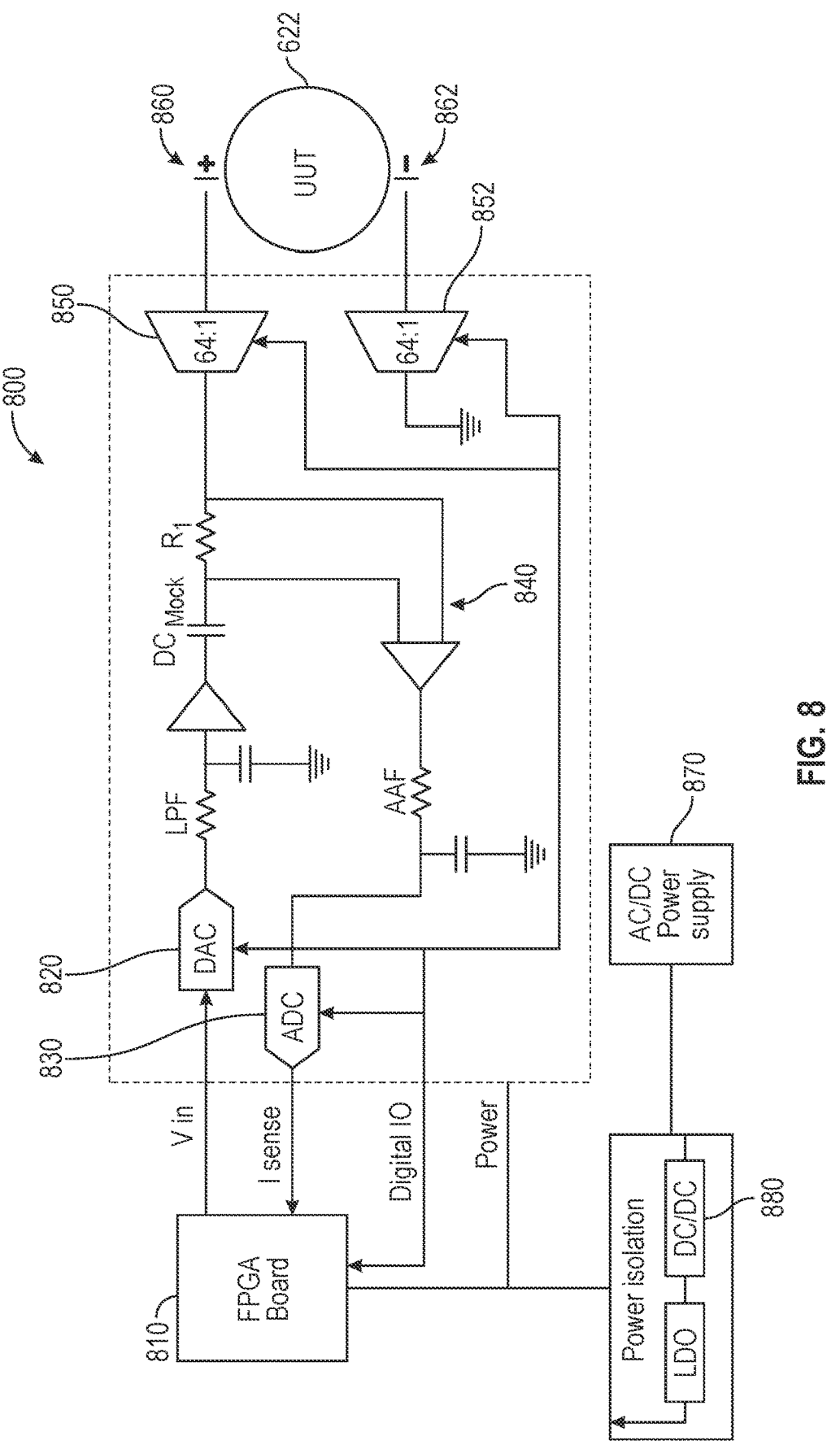
FIG. 8 is a schematic diagram of a voltage source circuit for an field programmable gate array (FPGA) board for use with the sensing system of FIG. 6.
Figure 9:
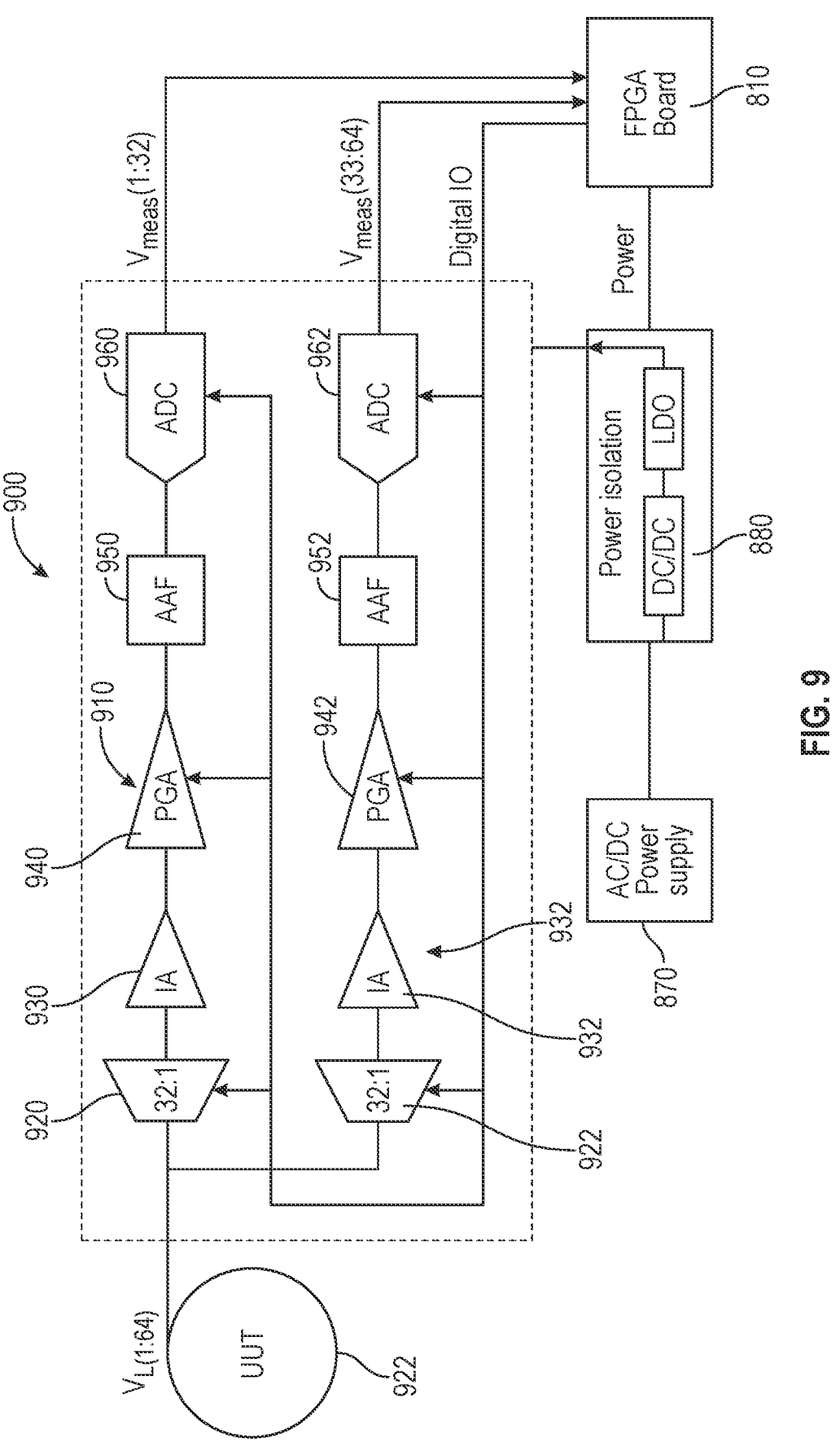
FIG. 9 is a schematic diagram of a voltage sensing circuit for an FPGA board of FIG. 8.

The circuitry of the EIT can incorporate a tetrapolar-based device that functions similarly to the above-described Sentech benchtop system using an integrated device that embeds a custom impedance analyzer with multiplexing to a 64-channel electrode array. With reference to FIG. 8, the small form-factor integrated system can be controlled by an off-board voltage-source module 800 that incorporates (e.g.) a Field Programmable Gate Array (FPGA) 810 with high speed communication and processing required for demodulating impedance signals. More particularly, for the wearable sensing arrangement herein, a custom impedance analyzer can be provided, including the above-described separate voltage source board 800 and a voltage sense (measurement) board 900 (FIG. 9) that interfaces through vertical interconnects. As shown further in FIG. 8, the voltage source board 800 can include a DAC 820 for arbitrary waveform generation, appropriate filtering, an ADC 830 and current sensing circuit 840, and two 1×64 MUX arrays 850, 852 to interface the positive and negative terminals 860, 862 of the voltage generated to 1 of 64 electrodes 622.

The exemplary voltage measurement board 900 (FIG. 9) can include two parallel 32-channel measurement circuits 910 and 912, which can desirably enable recording of single-ended voltage data from 64 channels in half the time it would take if a single 64-channel measurement circuit were used. Each measurement circuit 910, 912 respectively includes (e.g.) a 1×32 MUX 920, 922, an instrumentation amplifier (IA) 930, 932, programmable gain amplifier (PGA) 940, 942, antialiasing filter (AAF) 950. 952, and an analog to digital converter (ADC) 960, 962. The overall circuit(s) 800, 900 can receive AC/DC power from an appropriately rated power supply (or batteries) 870 via a power isolation circuit 880.

The NIRS and EIS data processing arranged by the FPGA board(s) 810 is adapted to receive ADC signals from both the EIS and NIRS modules 610, 620 (FIG. 6). These signals can be timestamped according to the system clock. Depending upon the implementation of the machine learning (ML) model, the FPGA can either connect directly to a server/processor (e.g., 200 in FIG. 2), where the data can be analyzed in a last recently used (LRU) fashion because of the predictive nature of the system.

It is contemplated in alternate embodiments of the system and method that a spectrometer/fiber based approach can be employed with associated optode cables constructed in a manner that are appropriately lightweight, robust and low-cost.

By way of non-limiting example, some of the various techniques and details presented herein are related to increase of the detected signal to brain tissue. Note that proper isolation of a brain tissue signal for use in validating and/or operating the system and method can employ optical reconstruction, which is a general term that describes the recovery of local changes in tissue optical properties at a predefined region from a measured signal containing contributions from multiple regions. Optical reconstruction forms the basis for imaging methods including diffuse optical tomography (DOT) and fluorescence molecular tomography (FMT), and is analogous in some ways to computed tomography (CT) and positron emission tomography (PET) reconstruction. The optical reconstruction forward problem is given generally by $\partial S_{\Omega} = \sum_{j=1}^{N_j} A_j [\mu_j] \partial \mu_j$, where $\mu_j$ represents the collective optical properties defined for $N_j$ spatial regions, and $\partial \mu_j$ is the local variations in optical properties responsible for the variation $\partial S_{\Omega}$ in the detected signal associated with the background properties $\mu_j$. The transformation between these two variations is given by $A_j$, also called the Jacobian. Optical reconstruction is performed by minimizing the difference between the experimental measurements of $S_{\Omega}$, and the predictions of the model based on an update equation. Essentially, all optical reconstruction methods can be broken down into four considerations: (i) selection of linear or nonlinear solver, (ii) definition of the signal domain, (iii) calculation of the Jacobian, and (iv) availability of a priori knowledge or "priors". The incorporation of priors into optical reconstruction is perhaps the most fertile ground for advances in quantitative DOT and FMT methods. The significance of priors can be understood from an algebraic perspective, in that optical reconstruction is an ill-posed and often underdetermined problem. Therefore, regularization (which is itself, fundamentally a prior in that it forces a solution with predetermined qualities—i.e. smoothness) and prior-based constraints are essential for converging to a unique solution. In recent years, a number of priors have been described and each has been implemented in a variety of different ways. For example, anatomical priors—information provided by an alternate imaging modality such as CT or magnetic resonance imaging (MRI)—can be implemented into the reconstruction process as a soft prior using Laplace regularization.

The ideal anatomical prior can comprise (e.g.) CT or MRI, or potentially clinical ultrasound, that provided a high-resolution volumetric dataset that could be segmented and meshed to provide a very accurate photon propagation model. However, the requirement of high-resolution medical imaging would obviously defeat the purpose of the proposed technology which is to provide bedside vigilance to a large group of patients who may or may not be ill, so that resources can be managed or directed towards those with suspected ongoing hemorrhage. In layered structures like the skin, subcutaneous fat and muscle within a small region, knowledge of the layer thicknesses alone could be sufficient to account for photon propagation variations, since light transport is highly diffuse. For example, absolute optical properties could be computed using a two-layered model of the human head from NIR broadband spectra acquired at three different distances, if the thickness of the top layer is known. Recent advances in ultrasound transducer technology make the acquisition of axial thicknesses using an integrated sensor simple and low-cost.

Priors can be generated using, for example, Capacitor Micromachined Ultrasound Transducers (CMUTs) emerged in the 1990s as an alternative to piezoelectric transducers (PZTs) that are found in conventional ultrasound devices. While PZTs remain superior in terms of efficiency and sensitivity for clinical imaging applications, CMUTs can actually provide better axial resolution and if lateral resolution can be sacrificed, they are superior in terms of coupling to skin (i.e., producing fewer undesirable issues with interface). Fabrication of CMUTs can be based on standard semiconductor fabrication processes, including micromachining using a combination of patterning tools, deposition tools and etching tools. The consequence of this fabrication process is two-fold: (a) significant cost reductions if stock patterns are used, due to existing semiconductor batch production infrastructure (economies of scale), (b) size reduction is substantial, where a piezoelectric transducer may require a composite structure of multiple millimeters, a 1-D CMUT array can be micrometers in thickness.

Figure 10:
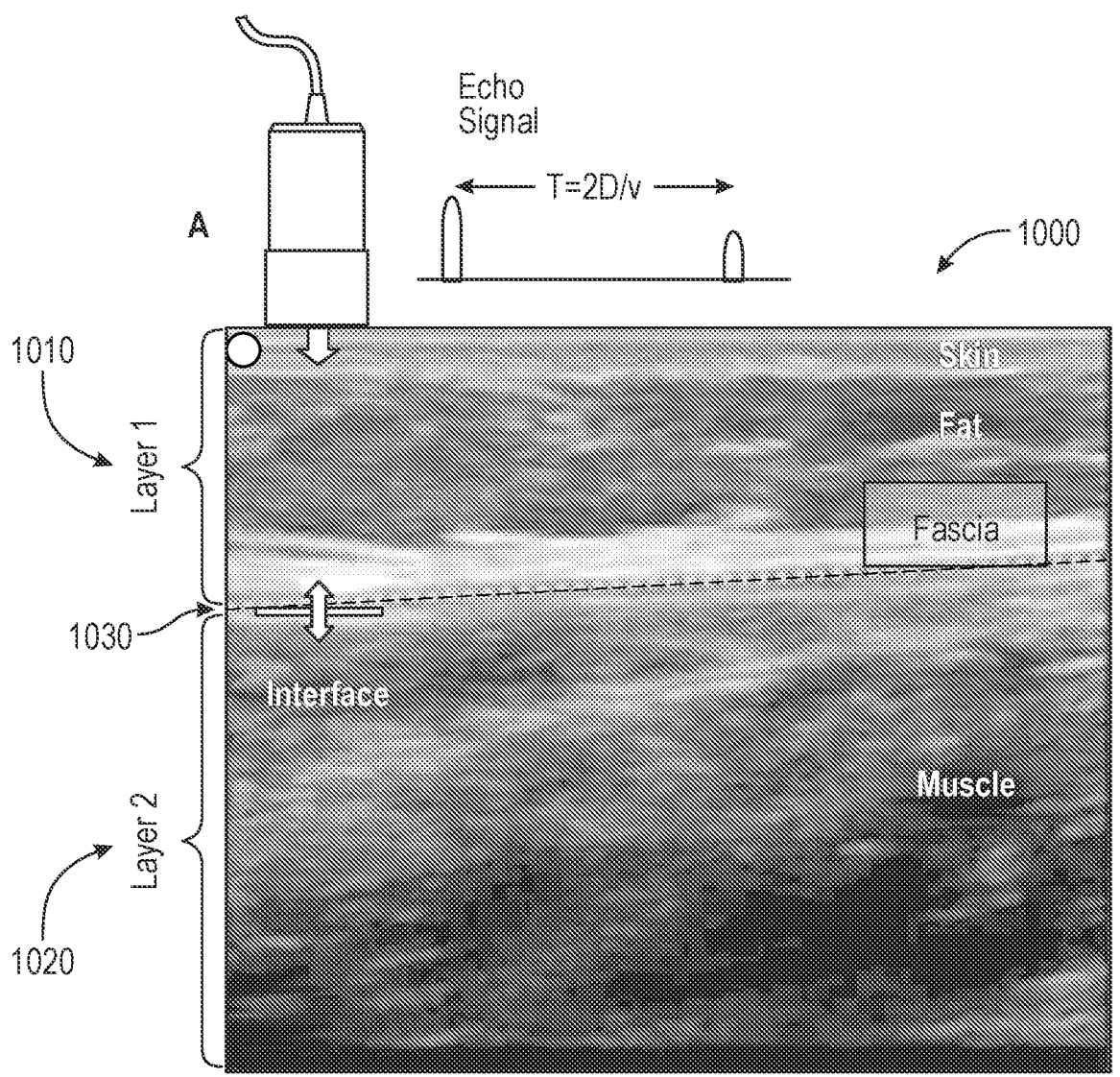
FIG. 10 is an ultrasound image acquired on an exemplary leg showing the layers of skin, subcutaneous fat (Layer 1) and muscle (Layer 2) that comprise typical appendicular muscle, to which the sensing device of FIG. 6 can be applied.
Figure 11:
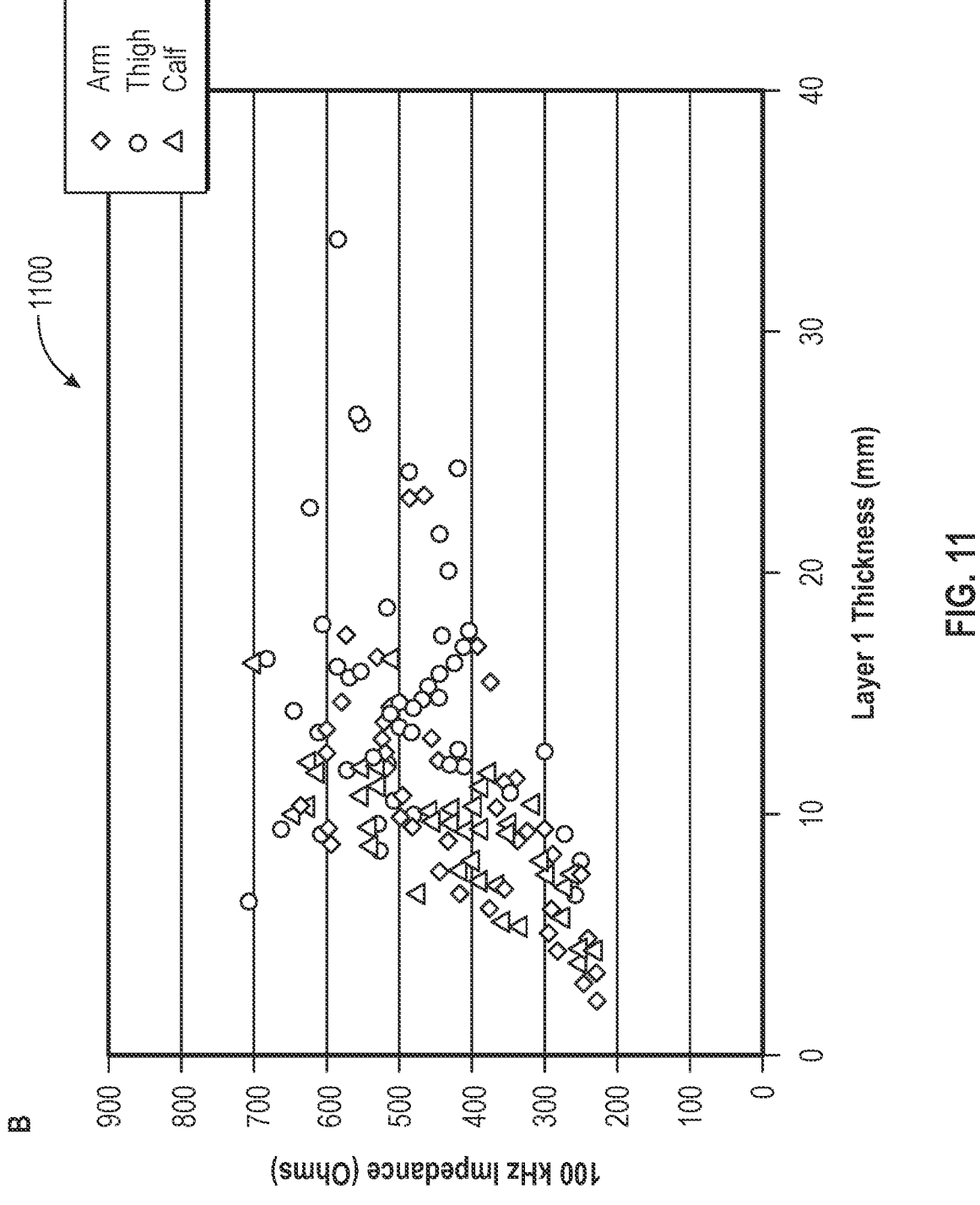
FIG. 11 is a graph plotting and exemplary relationship between impedance and the thickness of Layer 1 shown in the image of FIG. 10.
Figure 12A:
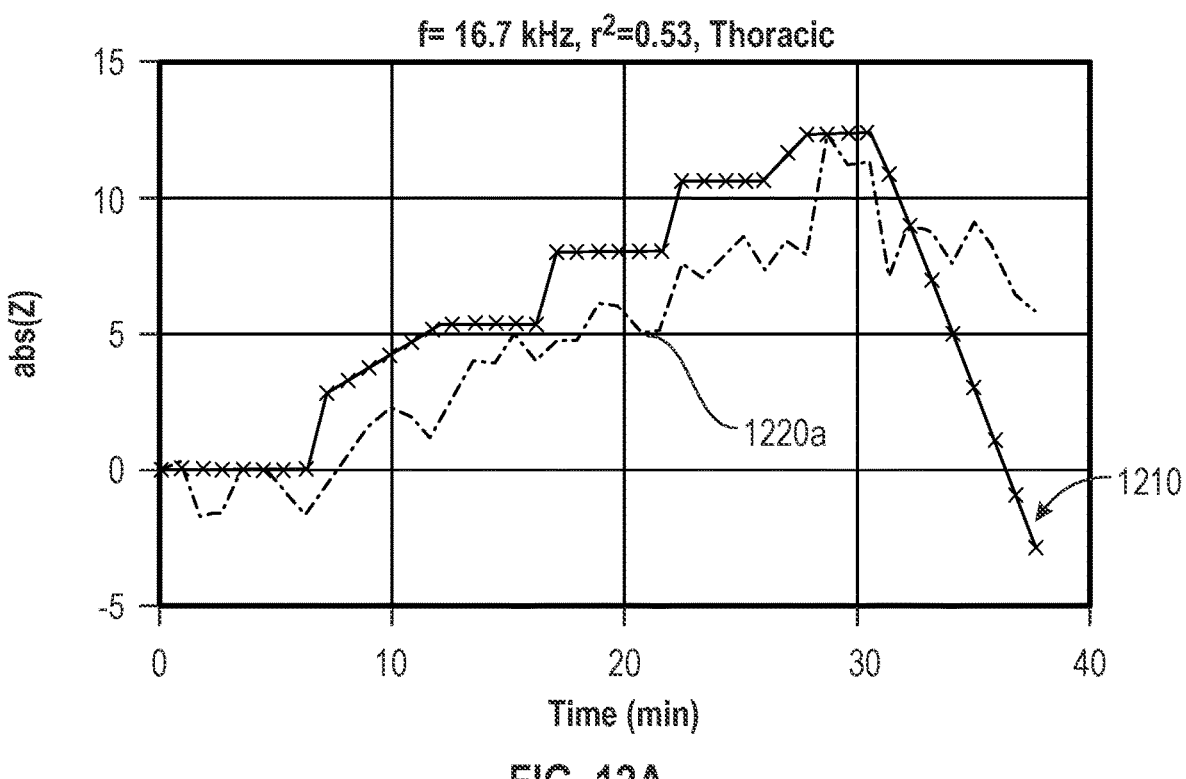
FIGS. 12A-12I depict various graphs of impedance magnitude (abs(Z)) vs. time, resistance (re(Z)) vs. time and reactance (im(Z)) vs. time as measured at three sites (thorax, abdomen, and arm) at differing frequencies f.
Figure 12B:
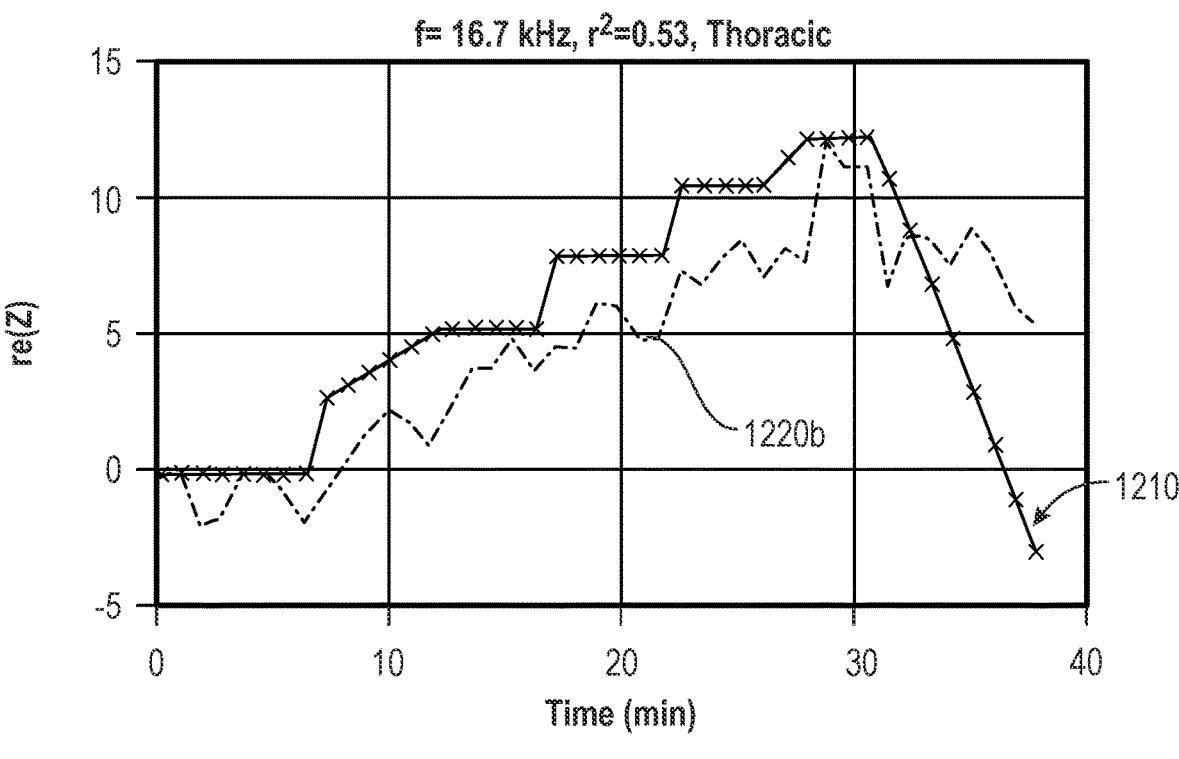
Figure 12C:
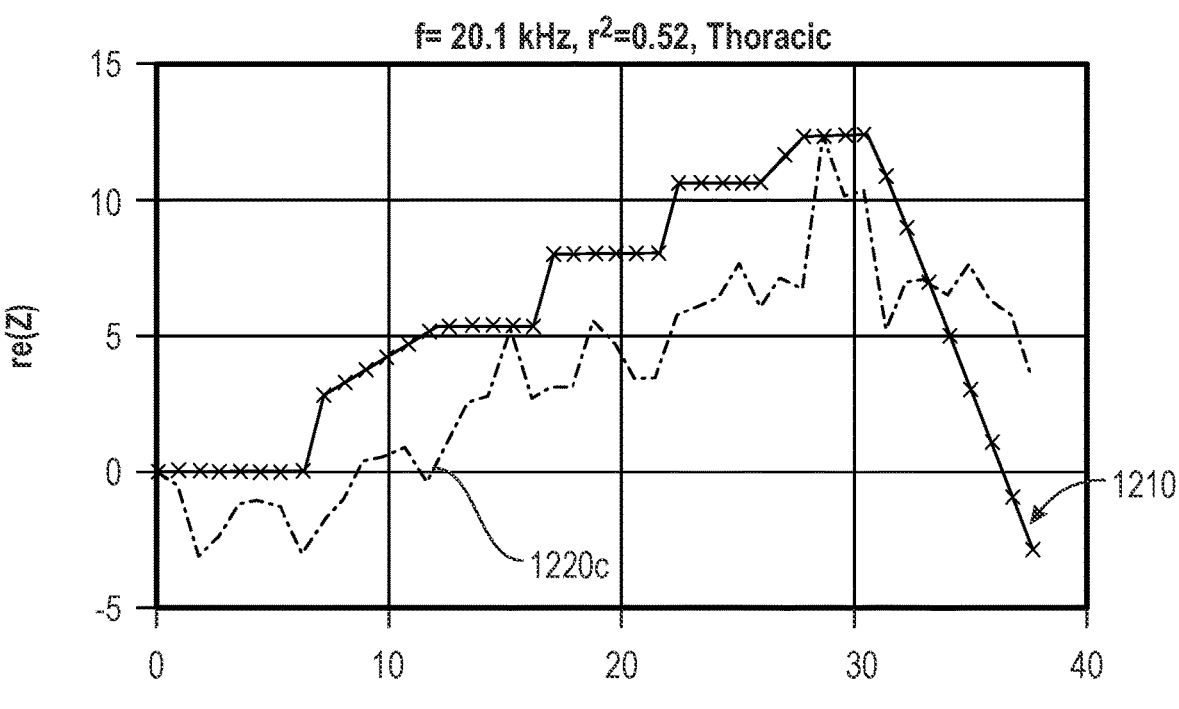
Figure 12D:
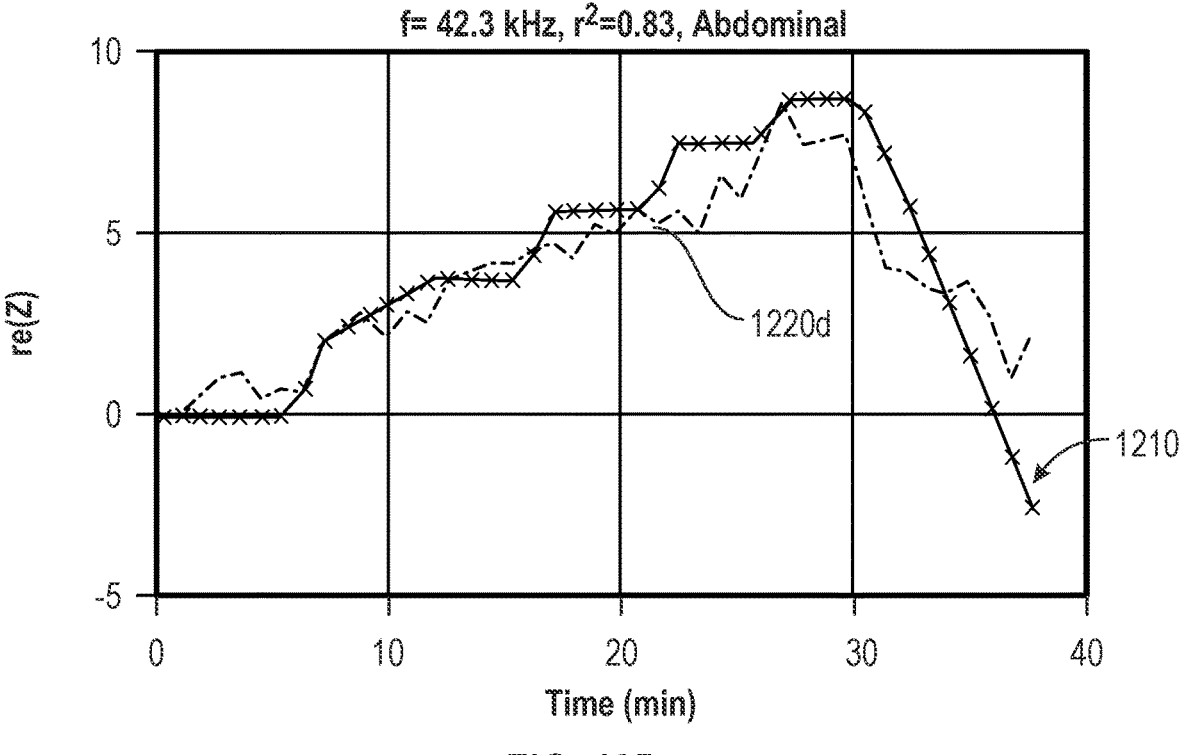
Figure 12E:
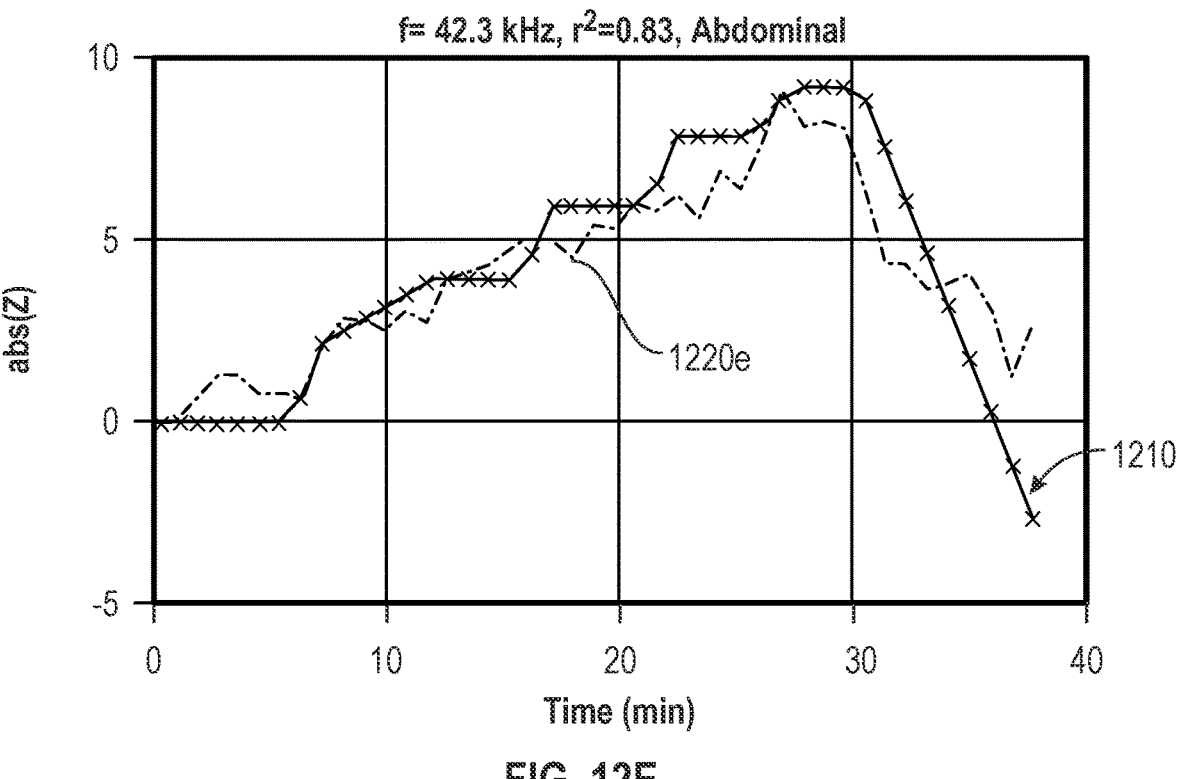
Figure 12F:
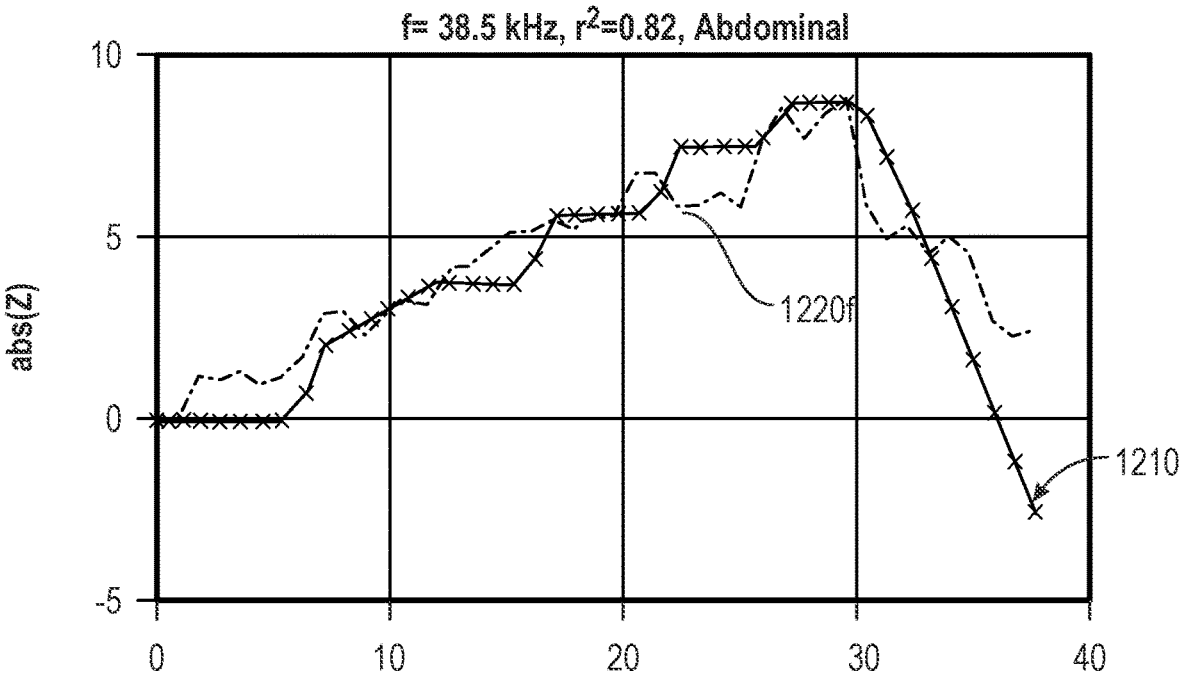
Figure 12G:
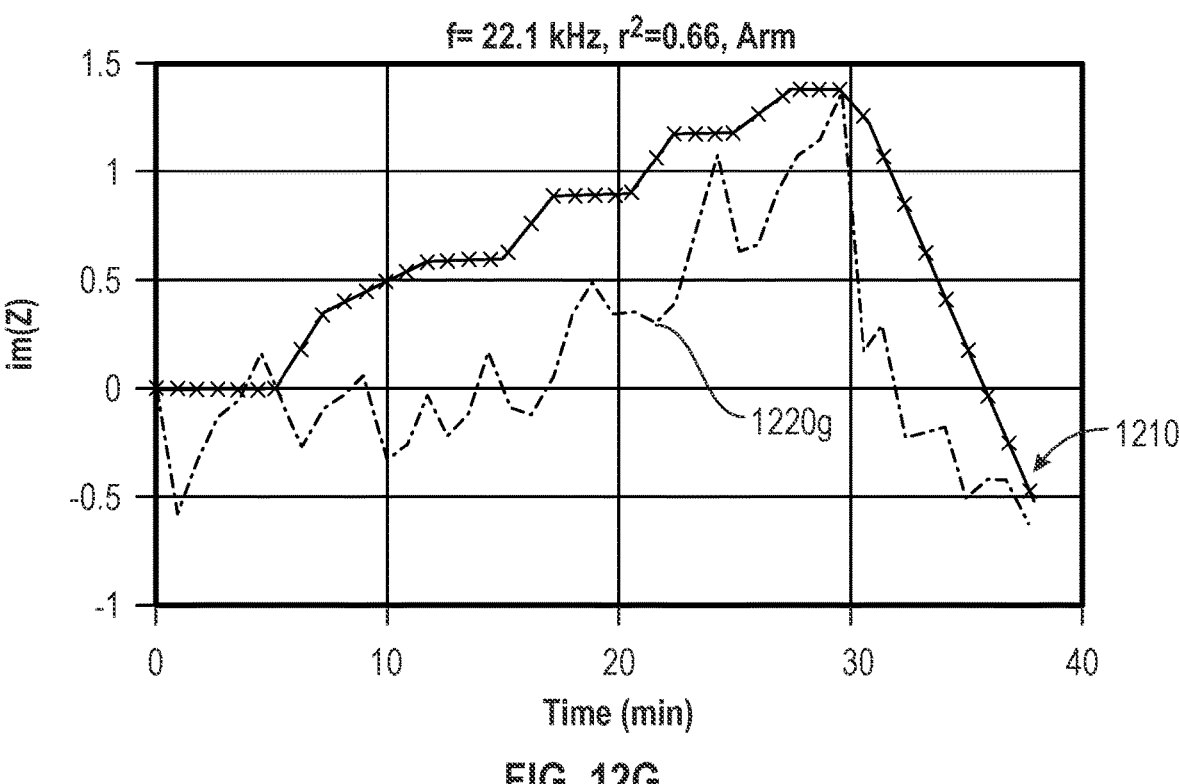
Figure 12H:
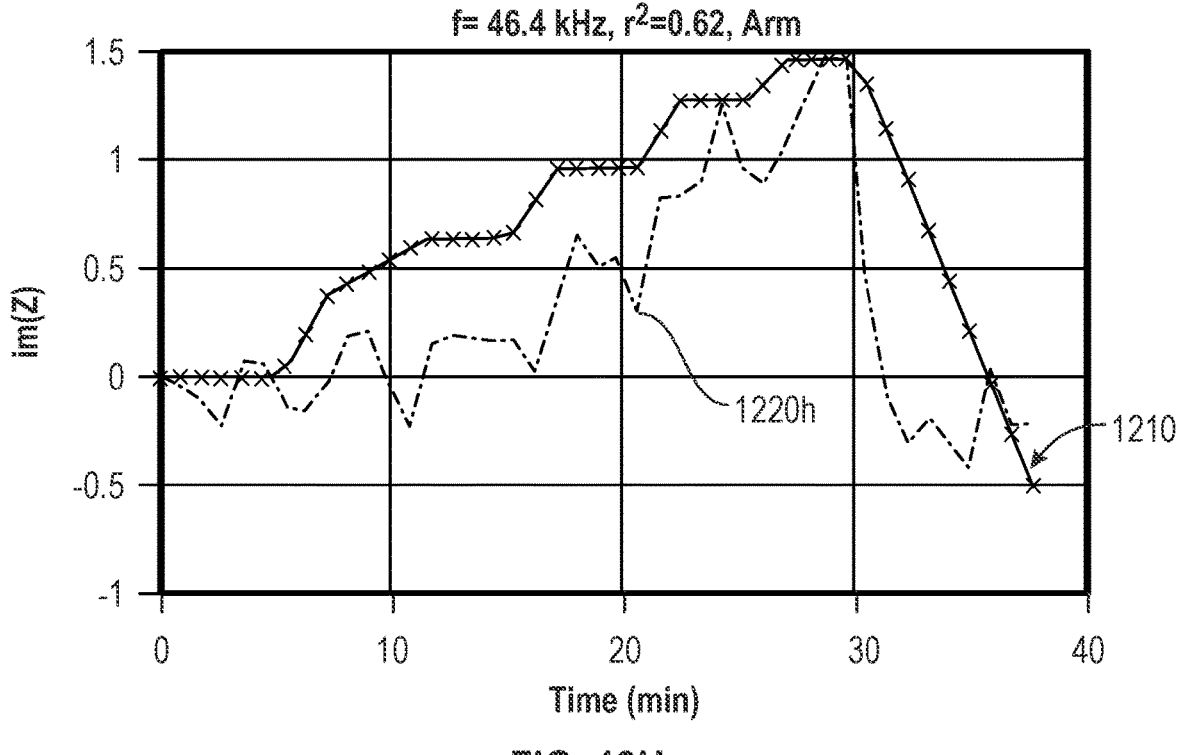
Figure 12I:
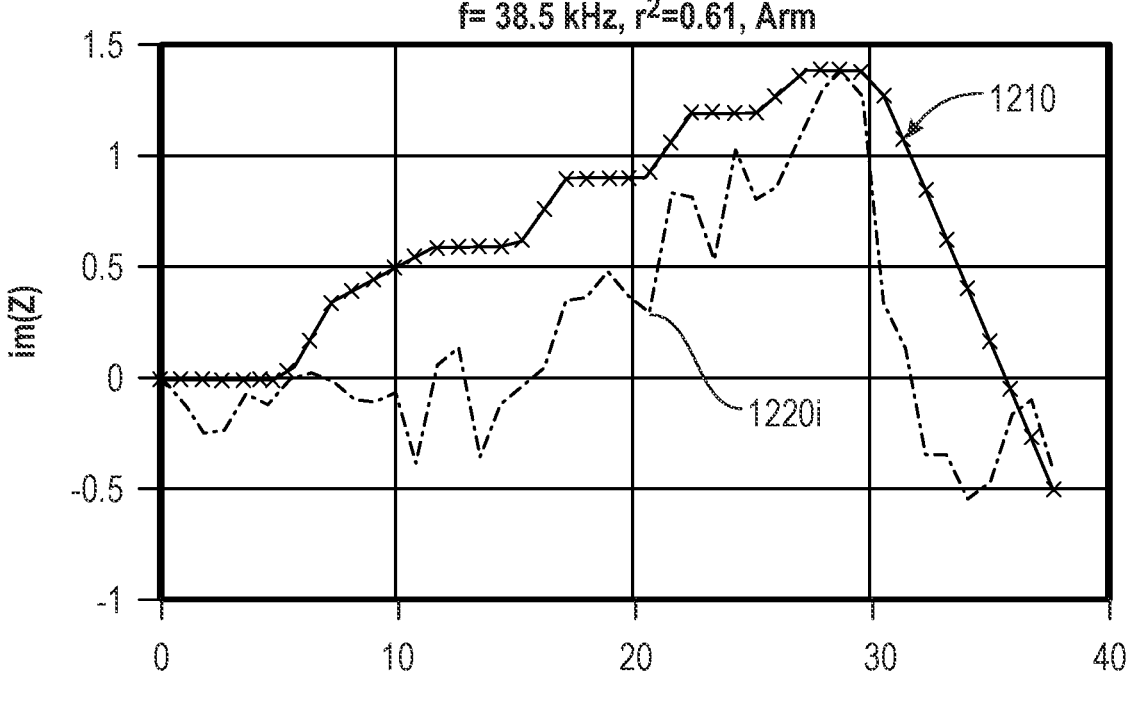

By way of further consideration in validating and operating the system and method, electrical impedance baseline correction can be employed as appropriate. The thickness of subcutaneous tissue has been shown to increase the electrical impedance. Reference is, thus, made to FIGS. 10 and 11, which, respectively show an exemplary ultrasound (US) image 1000 of leg tissue and a plot 1100 of impedance versus thickness for regions around an exemplary arm, thigh and calf (noting the high variability thereof) within the upper layer (Layer 1, below) of tissue in the image 1000. Note that the image 1000 (FIG. 10) defines two discrete layers, including Layer 1, composed of skin and subcutaneous fat 1010, and Layer 2, composed of muscle 1020, with an interface region 1030 therebetween. The thickness and content of such layers can vary widely from patient-to-patient and locations on a given patient's body. The first correction can entail application of a subcutaneous (SQ) thickness correction to reduce variation in electrical impedance. More generally U.S.-based information has previously been incorporated to improve the accuracy of EIT images in muscle imaging, and can be similarly used in implementation of the system and method to account for variable subcutaneous tissue content. It is noted that coupled US+EIT image reconstruction processes are particularly novel. In the illustrative embodiment, the use of soft-priors (i.e., anatomic information encoded into the EIT finite element method (FEM) mesh) for improving the accuracy and resolution of EIT images has been discussed, but not put into practice, and the foregoing represents the first time that a dual-modality system has been provided and combined with soft-prior image reconstruction for estimating (SQ) thickness. Note that the use of soft priors can be substituted with other appropriate techniques to improve accuracy in alternate embodiments of the system and method in a manner clear to those of skill. An appropriate mathematical computing procedure—such as the New Dartmouth Reconstruction MAT-LAB® software can be employed in the image reconstruction process. See for background information, Borsic, A., Halter, R., Wan, Y., Hartov, A. & Paulsen, K. D., Electrical impedance tomography reconstruction for three-dimensional imaging of the prostate. Physiological Measurement 31, S1 (2010). This procedure can employ and leverage US images to help guide image reconstruction. More particularly, US images can be segmented into skin, adipose (fat), and muscle layers using MATLAB-based image-processing routines. FEM meshes can then be constructed based on the segmented US images and the image reconstruction processes, along with soft-prior techniques, so as to produce 3D images of tissue. See for background information Murphy, E. K., Mahara, A. & Halter, R. J., A novel regularization technique for microendoscopic electrical impedance tomography. IEEE Transactions on Medical Imaging 35, 1593-1603 (2016); Murphy, E. K., Mahara, A., Wu, X. & Halter, R. J., Phantom experiments using soft-prior regularization EIT for breast cancer imaging. Physiological Measurement 38, 1262 (2017). See also, Murphy, Ethan K. Skinner, Joseph Mariucci, Maria Rutkove, Seward B. Halter, Ryan J., Towards Electrical Impedance Tomography Coupled Ultrasound Imaging for Assessing Muscle Health. IEEE Transactions on Medical Imaging, Vol 38, no. 9, pp. 1409-1419, 2018, by way of useful background information.

In implementing the system and method, it is contemplated that the variation in skin and subcutaneous fat thicknesses across human subjects, and along with measured skin pigmentation (by means of a photograph acquired with a ColorChecker card) can be compared to baseline values of NIRS and EIS. A two-layer NIRS model can be developed and allow determination of the error caused by no priors vs. BMI-indexed thickness vs. actual ultrasound-derived dimensions. This data can be employed in accordance with skill in the art to provide appropriate EIS correction to baseline.

IV. Operation of the System and Method

In a treatment environment with a patient, it is contemplated that the system and method can be deployed to detect OH and/or other systemic conditions. One or more sensing belts, and (optionally) other associated sensors that measure traditional vital signs (pulse, blood oxygen, heart rate, ECG, etc.), are applied to the patient-typically while in bed, or another stable position. The sensors are each interconnected to an appropriate input on the system control box, which can include a remote, or networked computing/interface device. The system is powered and the practitioner enters any needed identification and patient information, or links the device with a preexisting source of such data (e.g., an electronic patient chart) using appropriate inputs. After performing any needed initialization, including (e.g.) calibrating to the patient's vitals, the system begins to transmit data from appropriate sensors and sensing modalities. The information is transmitted to an appropriate display and/or data storage device so that the patient's current state can be continually monitored. The system and/or an interconnected computing device can include visual, audible and/or tactile alarms that notify personnel of any changes in condition or potentially troublesome conditions.

By way of non-limiting illustration, a plurality of enhancements to the algorithms/processes and data/telemetry outputs can be incorporated within the system. By way of non-limiting example, the system can operate multiple algorithms/processes simultaneously with each algorithm/process having been developed for optimal performance in different risk categories. Clinicians can thereby choose a low, medium, or high risk algorithm/process based the patient's clinical history and their bedside evaluation. As an additional refinement, clinicians can choose the algorithm/process output with respect to (e.g.) sensitivity, specificity, and positive and negative predictive value. By way of further non-limiting example, the clinician can have an initial impression that a patient is very low risk and choose a "low risk algorithm" with high specificity to prevent false positive alarms. Choice of algorithm/process could also reflect the clinical environment and resource limitations. As another additional refinement, the system can allow entering the various costs (such as the cost of false positives, the cost of treatment delay, etc.) by the physicians and provide optimal guidance on the patient prioritization strategy. As a non-limiting example, such optimal guidance can be developed using a stochastic dynamic programming model based, solved using (e.g.) backward induction or Q-learning in a manner clear to those of skill. Additionally, the output of the system may also display the measurements acquired from the diagnostic technologies plotted against time. This can allow clinicians to identify trends in the data that do not meet the diagnostic or prognostic thresholds of the algorithm(s)/process(es).

The multivariable algorithms that transform the data streams into a clinically useful output may be patient independent, having been empirically derived from broad data sets, or, alternatively patient specific based on "change from baseline" heuristics. In the latter method, clinicians may define a patient as "without disease" (i.e. no OH) when the device is first applied. This would become the baseline measurements set, and the algorithm would alarm when a predetermined "change from baseline" has occurred. The change from baseline may be user definable based on one or more of: clinician preference, local epidemiology, event circumstances such as the method of trauma, other user definable criteria.

Of particular importance, this device may be attached the patient, or connected to the patient via wireless technology, and will remain fully vigilant to changes in the overall pattern of signals. These patterns may be transformed via a prederived algorithm and the device may alarm when thresholds of disease probability have been met. Clinicians cannot, for reasons of limited resources or human factors, cannot maintain such a level of vigilance or continuously incorporate such multivariable analyses.

V. EIS and EIT Measurements

FIGS. 12A-I depict various graphs of impedance magnitude (abs(Z)) vs. time, resistance (re(Z)) vs. time and reactance (im(Z)) vs. time as measured at three sites (thorax, abdomen, and arm) at differing frequencies f. Also depicted on the graphs is increasing lower body negative pressure (LBNP) applied over time. These results demonstrate that the relative (delta) comparison of EIT and EIS data dramatically outperform the standard vital signs. The improvement due to the relative comparison removes inter-subject variability, but the very high AUC of 0.99 from the initial LBNP increase from 0-to-15 mmHg for the EIT data was a surprising and unexpected result.

A. Methodology

A recipient is fitted with two EIT belts. For example, the two belts can be fitted at and around: (a) the thorax at the point of maximum impulse and (b) the abdomen, just above the umbilicus. The belts can be according to the examples of FIG. 6 or 7. The EIS were recorded on the thorax, abdomen, and arm, via placed electrodes.

A 4-point measurement is performed wherein a current (I) is injected between two electrodes. The current (I) can be any current value, and in one example is imperceptible to the recipient. The voltage difference (V) is recorded on two other electrodes, which yields the impedance (Z=V/I). Electrical impedance can be measured over a range of frequencies, i.e., electrical impedance spectroscopy (EIS), at different sites on the body, and multiple electrical impedances from 98 different electrode combinations from 16-electrode belts wrapped around the subject at a fixed radiant distance.

The belt electrical impedance data can be combined to produce an image of electrical properties using a method referred to as electrical impedance tomography (EIT). Compared to skin-based optical technologies, EIS and EIT obtain signals from a larger volume of tissue. EIT has been considered for numerous medical applications including ventilation and lung mechanics assessment, pneumothorax detection, brain imaging, cancer detection, stroke volume variation, and brain or abdominal bleeds.

In this example, the effect of loss of blood fraction of tissue measured by EIS or EIT (i.e. subtle reduction in tissue conductivity by blood loss) was detected.

The data that formed FIGS. 12A-I resulted from 18 healthy subjects undergoing increasingly lower body negative pressure (LBNP) as a mimic of hemorrhage. LBNP mimics acute hemorrhage by drawing intravascular volume out of central circulation and into the legs.

As discussed above, two EIT belts were placed around: (a) the thorax at the point of maximum impulse and (b) the abdomen, just above the umbilicus, while the EIS measurements were recorded on the thorax, abdomen, and arm. The EIT data (recorded at 150 kHz) was analyzed in terms averages of five groups of impedance values (EIT-groups). Specifically, the groups were formed by four clusters of similar magnitude impedances that naturally form from the full set of 98 impedance values and additionally a group of all 98 impedance values. The EIS data included 3 sites (noted above: thorax, abdomen, and arm) and recorded the resistance (re(Z)) and reactance (im(Z)) at 100 logarithmically-spaced frequencies from 100 Hz to 1 MHz. Additionally, the magnitude (|Z|) and phase (ph(Z)) at each frequency were considered.

In addition to EI, subjects underwent continuous measurement of mean aortic pressure (MAP) measured on the brachial artery, single-channel photoplethysmography, and Electrocardiography (EKG) monitoring. For analysis of physiological measurements, the parameters reported are 1) MAP, 2) area-under the curve from trough-to-trough of photoplethysmography waveforms (Pleth), and 3) beat-to-beat HR.

The LBNP was transitioned from 0 to 60 mmHg in 15 mmHg increments, as tolerated, then 60 to 100 in 10 mmHg increments, with pressure being held constant on average for 4.2 minutes at each step. To focus on simulated occult hemorrhage, we report on data corresponding to LBNP values from 0 to 45 mmHg during which there is generally a limited change in vital signs. Bleed versus no-bleed states are compared in two ways.

First, an absolute comparison is performed between the data at LBNP=15, 30, and 45 mmHg (bleed states) and LBNP=0 (no bleed). Second, a relative (delta) comparison is performed between data changes between 0-to-15, 15-to-30, and 30-to-45 mmHg LBNP (bleed-state changes) and the change in the last two minutes of LBNP=0 (no bleed). For both comparisons we report on the area-under-the-curve (AUC) from receiver-operator-characteristic (ROC) curve corresponding to the best parameters of each technique type. All data were averaged to be per-minute sample rates.

B. Results

EIT and EIS AUCs were (0.50, 0.55, 0.61) and (0.53, 0.56, 0.58), respectively, for LBNP values of 15, 30, and 45 mmHg. The vital-sign AUCs for MAP, Pleth, and HR were (0.51, 0.51, 0.51), (0.62, 0.57, 0.73), and (0.60, 0.56, 0.76) for LBNP values of 15, 30, and 45 mmHg respectively.

EIT and EIS AUCs were (0.99, 0.95, 1.00) and (0.86, 0.89, 0.92) for the bleed-state changes from 0-to-15, 15-to-30, and 30-to-45 mmHg. The vital-sign AUCs for MAP, Pleth, and HR were (0.54, 0.53, 0.54), (0.75, 0.53, 0.75), and (0.75, 0.73, 0.80), respectively, for the bleed-state changes from 0-to-15, 15-to-30, and 30-to-45 mmHg. For both the absolute and relative comparison, the best EIT-group corresponds to the second smallest magnitude group from the thorax belt and the best EIS results correspond to the thorax site in terms of re(Z) at 9.5 kHz. The delta electrical impedance 1220a-i performs so well in detection of LBNP progression that its graph essentially mimics the progressive increase in LBNP progression 1210, as shown in FIGS. 12A-12I.

Pleth and HR have an initial change in one direction (0-to-15 mmHg) followed by a larger change in the opposite direction for larger LBNP values. For instance, initially there is a small drop in HR and then an (expected) larger increase in HR for larger LBNP values.

V. Conclusion

It should be clear that the multivariable poly-anatomic system and method for generating and analyzing various forms of physiological and anatomical information provides a robust and desirable mechanism for evaluating and monitoring potentially life-threatening conditions, such as OH. The novel system and method effectively combines different types of analyses into a single device, —for example EIS and NIRS. Measurements generated by the system and method can be refined using existing medical data that is processed with advanced computing procedures—such as classical machine learning, ensemble learning or other AI-based approaches.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or sub-processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g., 1-5 percent). Accordingly, this description is meant to be taken only by way of example, and not to otherwise limit the scope of this invention.

What is claimed is:

1. A system for detecting an internal condition in a living body comprising:

an polyanatomic sensing belt having a plurality of skin contactable sensors that each respectively generate one or more types of sensor data with respect to anatomical functions, the plurality of skin contactable sensors including a plurality of electrical impedance tomography (EIT) sensors, near-infrared spectroscopy (NIRS) sensors, and electrical impedance spectroscopy (EIS) sensors, each of the skin contactable sensors being constructed and arranged to respectively provide a data stream so that polyanatomic patterns can be derived, wherein the belt defines a relative contacted skin location on the body for each of the plurality of skin contactable sensors;

a controller integrated with the belt and configured to synchronize data in the respective data streams from the plurality of skin contactable sensors and to deliver the synchronized data in a multi-anatomic data stream to a processor; and a data analysis process running on the processor, the data analysis process correlated to a degree of risk for the internal condition based on a clinical history and bedside evaluation of a wearer of the polyanatomic sensing belt, the data analysis process processing each data point in the synchronized multi-anatomic data stream as a localized quantum particle moving in a quantum potential representative of density of tissue of the body, and provides an output indicative of a probability that the internal condition is associated with a current or future disease state based on distinctions of sensed muscle tissue data from sensed subcutaneous tissue data resulting from the processing of the synchronized multi-anatomic data stream as localized quantum particles moving in a quantum potential representative of density of tissue of the body.

2. The system as set forth in claim 1 wherein the internal condition is related to ongoing occult hemorrhage (OH).

3. The system as set forth in claim 1 wherein the synchronized multi-anatomic data stream further includes information from at least one of: classic medical vital signs, photoplethysmography or an ECG.

4. The system as set forth in claim 1 wherein the data analysis process includes a machine learning processor that performs feature extractions and supervised learning and thereby generates metaclassifiers.

5. The system as set forth in claim 4 wherein the machine learning processor defines a deep neural network.

6. The system as set forth in claim 5 wherein the deep neural network comprises at least one of a convolutional neural network (CNN), an recurrent neural network (RNN), and an Long short-term memory (LSTM).

7. The system as set forth in claim 1 further comprising a refining process that increases accuracy of the data stream based upon priors.

8. The system as set forth in claim 1, wherein the data analysis process is constructed and arranged to operate multiple analysis processes concurrently, wherein each of the analysis processes is adapted to provide optimized performance in each of multiple, discrete different risk categories, respectively.

9. The system as set forth in claim 8 wherein the analysis process includes a clinician-selectable process adapted to provide varying sensitivity and specificity.

10. The system as set forth in claim 1 further comprising a system output display showing a combination of analysis process results and actual multiplex measurements that are inputs to the analysis process, both plotted against time.

11. The system as set forth in claim 1, wherein the processor provides optimal guidance for configuring the data analysis process based on a cost of false positives and on a cost of treatment delay using a stochastic dynamic programming model using backward induction or Q-learning.

12. A medical treatment method using the system of claim 1, the method comprising the steps of:

applying a plurality of polyanatomic sensing belts to the body at predetermined locations, including thorax and limbs; and operating the sensors and the processor on a substantially continuous basis to generate the output.

13. The medical treatment method as set forth in claim 12 wherein the internal condition is related to occult hemorrhage, an infectious process, or cardiovascular dysfunction.

14. A system for determining a probability that an internal condition in a living body is associated with a current or future disease state comprising:

a polyanatomic sensing belt having a plurality of wearable sensors that each respectively monitor one or more types of anatomical functions, the plurality of wearable sensors including a plurality of electrical impedance tomography (EIT) sensors, near-infrared spectroscopy (NIRS) sensors, and electrical impedance spectroscopy (EIS) sensors, each of the wearable sensors being constructed and arranged to respectively provide a data stream representative of a monitored anatomical function for polyanatomic pattern detection, wherein the belt defines a relative contacted skin location on the body for each of the plurality of wearable sensors;

a controller system integrated with the belt and configured to synchronize data in the respective data streams from the plurality of wearable sensors and to deliver the synchronized data in a multi-anatomic data stream for polyanatomic pattern detection; and a processor executing a data analysis process correlated to a degree of risk for the internal condition based on a clinical history and bedside evaluation of a wearer of the polyanatomic sensing belt that:

processes each data point in the multi-anatomic data stream as a localized quantum particle moving in a quantum potential representative of tissue density;

distinguishes sensed muscle tissue data from sensed subcutaneous tissue data; and provides an output indicative of a probability that the internal condition is associated with a current or future disease state based on the sensed muscle tissue data as distinguished from the sensed subcutaneous tissue data.

15. The system as set forth in claim 14 wherein the processor provides optimal guidance for configuring the data analysis process based on a cost of false positives and on a cost of treatment delay using a stochastic dynamic programming model using backward induction or Q-learning.

16. The system as set forth in claim 14 wherein the data analysis process includes a machine learning processor that performs feature extractions and supervised learning and thereby generates metaclassifiers.

17. The system as set forth in claim 16 wherein the machine learning processor defines a deep neural network.

18. The system as set forth in claim 17 wherein the deep neural network comprises at least one of a convolutional neural network (CNN), an recurrent neural network (RNN), and an Long short-term memory (LSTM).

19. The system as set forth in claim 14 further comprising a refining process that increases accuracy of the data stream based upon priors.

20. The system as set forth in claim 14, wherein the data analysis process is constructed and arranged to operate multiple analysis processes concurrently, wherein each of the analysis processes is adapted to provide optimized performance in each of multiple, discrete different risk categories, respectively.

\* \* \* \* \*